United States Patent [19]

Buckle et al.

[11] Patent Number: 5,470,872
[45] Date of Patent: Nov. 28, 1995

[54] BENZOPYRANOLS

[75] Inventors: Derek R. Buckle; Ivan L. Pinto; David G. Smith, all of Epsom, England

[73] Assignee: Beecham Group plc, England

[21] Appl. No.: 166,612

[22] Filed: Dec. 14, 1993

Related U.S. Application Data

[63] Continuation of Ser. No. 449,577, Dec. 12, 1989, abandoned.

[30] Foreign Application Priority Data

Dec. 13, 1988 [GB] United Kingdom ............... 8829066
Apr. 25, 1989 [GB] United Kingdom ............... 8909381
Jun. 20, 1989 [GB] United Kingdom ............... 8914096

[51] Int. Cl.⁶ .................... A61K 31/35; C07D 311/04
[52] U.S. Cl. ................... 514/456; 514/212; 514/320; 549/399; 549/404; 548/525; 546/196
[58] Field of Search ............... 546/196; 548/525; 549/399, 404; 514/320, 212, 456

[56] References Cited

U.S. PATENT DOCUMENTS

| | | | |
|---|---|---|---|
| 4,786,639 | 11/1988 | Evans ........................ | 514/254 |
| 5,032,591 | 7/1991 | Evans et al. .................. | 514/254 |
| 5,032,596 | 7/1991 | Williams ..................... | 514/302 |
| 5,053,427 | 10/1991 | Stemp et al. ................. | 514/456 |

FOREIGN PATENT DOCUMENTS

| | | | |
|---|---|---|---|
| 076075 | 4/1983 | European Pat. Off. ........... | 546/207 |
| 093535 | 11/1983 | European Pat. Off. ........... | 546/207 |
| 250077 | 12/1987 | European Pat. Off. ........... | 514/254 |
| 0296975 | 6/1988 | European Pat. Off. ........... | 546/207 |
| 273262 | 7/1988 | European Pat. Off. ........... | 514/254 |
| 314446 | 5/1989 | European Pat. Off. ........... | 514/254 |

*Primary Examiner*—Robert T. Bond
*Attorney, Agent, or Firm*—Rosenman & Colin

[57] ABSTRACT

Novel Compounds

A compound of formula (I):

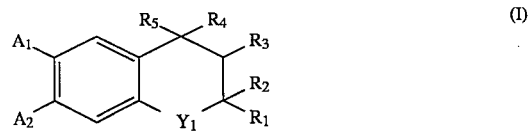

where the substituents are defined later in the specification. The compounds are useful as muscle relaxants and as such have a number of pharmaceutical uses.

36 Claims, No Drawings

BENZOPYRANOLS

This application is a continuation of Ser. No. 07/449,577 filed 12 Dec. 1989, now abandoned.

This invention relates to certain novel compounds, in particular novel benzopyran derivatives, to processes for their preparation, to compositions containing such compounds and to the use of such compounds and compositions in medicine.

European Patent Applications, Publication Numbers 76075, 93535, 95316, 107423, 120426, 126311, 126350, 126367, 138134, 250077, 273262 and 298452 describe certain benzopyran derivatives having inter alia antihypertensive activity. EP-A-176689 also discloses that certain benzopyran derivatives are useful for the treatment of inter alia disorders of the respiratory system.

European Patent Application, Publication Number 314446 also discloses certain benzopyran derivatives used in the treatment of hypertension, this disclosure is relevant to the present application only by virtue of Article 54(3) EPC.

A group of novel benzopyran derivatives has now been discovered which surprisingly has smooth muscle relaxant activity, and such compounds are therefore potentially useful as bronchodilators in the treatment of disorders of the respiratory tract, such as reversible airways obstruction and asthma, and also in the treatment of hypertension. Such compounds are also indicated to be of potential use in the treatment of disorders associated with smooth muscle contraction of the gastro-intestinal tract, uterus or the urinary tract including the ureter. Such disorders respectively include irritable bowel syndrome and diverticular disease; premature labour; incontinence; renal cholic and disorders associated with the passage of kidney stones. They are also indicated as of potential use in the treatment of cardiovascular disorders other than hypertension, such as congestive heart failure, angina, peripheral vascular disease and cerebral vascular disease; and also in the treatment and/or prophylaxis of disorders associated with pulmonary hypertension and of disorders associated with right heart failure.

These compounds are also indicated to have potential use as anti-convulsants in the treatment of epilepsy.

Accordingly, the present invention provides a compound of formula (I):

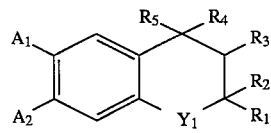

or, where appropriate, a pharmaceutically acceptable salt thereof, or a pharmaceutically acceptable solvate thereof wherein:

one of $A_1$ or $A_2$ represents hydrogen and the other represents a group $CF_3$—Y— wherein Y represents —$CF_2$—, >C=O, or —CH(OH)—;

$Y_1$ represents —O—, —$CH_2$— or $NR^o$ wherein $R^o$ is hydrogen, alkyl or alkylcarbonyl; $R_1$ and $R_2$ independently represent hydrogen or alkyl; or $R_1$ and $R_2$ together represent a $C_{2-7}$ polymethylene moiety;

$R_3$ represents hydrogen, hydroxy, alkoxy or acyloxy and $R_4$ is hydrogen or $R_3$ and $R_4$ together represent a bond;

$R_5$ represents either a moiety of formula (a):

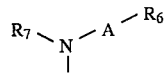

wherein A represents >C=X wherein X is O, S or $NR_8$ wherein $R_8$ represents CN, $NO_2$, $COR_9$ wherein $R_9$ is alkyl, amino, monoalkylamino, fluoroalkyl, phenyl or substituted phenyl or $R_8$ is $SO_2R_9$ wherein $R_9$ is as defined above, or A represents a bond; when A represents >C=X wherein X is O or S, then $R_6$ is hydrogen; alkyl optionally substituted by one or more groups or atoms selected from halogen, hydroxy, alkoxy, alkoxycarbonyl, carboxy or an ester or amide thereof, amino, monoalkylamino or dialkylamino; alkenyl; amino optionally substituted by an alkyl or alkenyl group or by an alkanoyl group optionally substituted by up to three halo atoms, by a phenyl group optionally substituted by alkyl, alkoxy or halogen; substituted or unsubstituted aryl or substituted or unsubstituted heteroaryl; and $R_7$ represents hydrogen or alkyl; or $R_6$ and $R_7$ together represent a linking chain of formula —$A_3$—$A_4$—, $A_3$ being attached to the nitrogen atom of the moiety —N—A— and $A_4$ being attached to the group A on the said moiety, and wherein $A_3$ represents a substituted or unsubstituted methylene group, $A_4$ represents 2 or 3 linking members, one of the linking members optionally representing O, S or NR and the other linking members each independently representing a substituted or unsubstituted methylene group; R represents hydrogen, alkyl, alkanoyl, phenyl $C_{1-4}$-alkyl, arylcarbonyl wherein the aryl group may be substituted or unsubstituted; or R is mono- or bi-cyclic- heteroarylcarbonyl;

when A represents >C=X wherein X represents $NR_8$, then $R_6$ represents —$NH.R_{10}$ wherein $R_{10}$ is hydrogen, alkyl, $C_{3-6}$ cycloalkyl, alkenyl or alkynyl and $R_7$ is hydrogen or alkyl; or $R_7$ and $R_{10}$ together represent $C_{2-4}$ polymethylene;

when A represents a bond, then $R_6$ and $R_7$ together with the nitrogen atom to which they are attached, form an unsaturated heterocyclic ring having 5 to 7 ring atoms, which ring atoms comprise up to 2 further nitrogen atoms and a carbon atom, the carbon atom being substituted with either an oxo group or a thioxo group, the remaining ring atoms being substituted or unsubstituted;

or $R_5$ represents a moiety of formula (b):

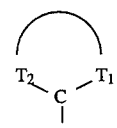

wherein $T_1$ represents >C—OH or $N(O)_n$ wherein n is zero or 1 and $T_2$ together with C—$T_1$, when $T_1$ is >C—OH, represents an optionally substituted aryl group or $T_2$ together with $CT_1$, when $T_1$ is $N(O)_n$, represents an optionally substituted, N- heteroaryl group;

or $R_5$ represents a moiety of formula (c):

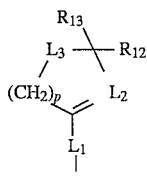

(c)

wherein L₁ represents O or NR₁₁ wherein R₁₁ represents hydrogen, alkyl, formyl, acetyl or hydroxymethyl, L₂ represents N or CL₄ wherein L₄ is hydrogen, halogen, formyl or hydroxymethyl, L₃ represents CH₂, O, S, >CHL₅ wherein L₅ is halogen or NL₆ wherein L₆ is hydrogen or alkyl and R₁₂ and R₁₃ each independently represent hydrogen or alkyl or R₁₂ together with R₁₃ represents oxo or thioxo; and p represents 1,2 or 3.

Suitably, A₁ represents CF₃—Y— and A₂ represents hydrogen.

Suitably, Y represents —CF₂— or —CH(OH)—.

Preferably, Y represents —CF₂—

Thus, preferably, A₁ represents C₂F₅ and A₂ represents H.

Preferably, Y₁ represents —O—.

When R₄ is hydrogen, it is favoured if R₃ represents hydrogen, hydroxy or acyloxy especially hydroxy.

Suitably, R₅ represents a moiety of formula (a).

When R₅ represents a moiety (a) one favoured subgroup of compounds are those wherein A represents >C=X wherein X is O or S, especially O, and R₆ together with R₇ represents a linking chain —A₃—A₄— as defined above.

Preferably, A₃ represents an unsubstituted methylene group.

Preferably, A₄ represents —CH₂CH₂— or —CH₂CH₂CH₂— especially —CH₂CH₂CH₂—.

When the linking chain —A₃—A₄— comprises substituted methylene groups it is favoured if one or two of methylene groups are substituted, in particular it is favoured if the methylene group represented by —A₃— is substituted.

Suitable substituents for any methylene group in —A₃—A₄— include alkyl groups, especially methyl or ethyl and in particular methyl.

In one particular aspect when A represents >C=X, the linking chain —A₃—A₄— (and thus R₆ and R₇ together) represent a moiety of formula —CH₂—(CH₂)_q—Z—(CH₂)_r— wherein q and r are 0 to 2 such that q+r is 1 or 2 and Z is CH₂, O, S or NR wherein R is as defined above.

Suitably R represents hydrogen, C₁₋₉ alkyl, C₂₋₇ alkanoyl, phenyl-C₁₋₄- alkyl, naphthylcarbonyl, phenylcarbonyl or benzylcarbonyl optionally substituted in the phenyl or naphthyl ring by one or two of C₁₋₆ alkyl, C₁₋₆ alkoxy or halogen; or R is mono- or bi-cyclic- heteroarylcarbonyl.

When A represents a bond, suitable unsaturated, heterocyclic rings represented by the moiety R₇.N.R₆ include 5- or 6- membered rings, favourably 6- membered rings.

Suitable optional substituents for the ring atoms of the unsaturated, heterocyclic ring represented by R₇.N.R₆ include alkyl, hydroxyl, halogen, alkoxy, alkanoyloxy, nitro, amino, acylamino, carboxy or alkoxy carbonyl.

Suitably, R₆ and R₇ together with the nitrogen atom to which they are attached, form a substituted or unsubstituted pyridonyl group or a substituted or unsubstituted thiopyridonyl group.

Suitably the moiety R₇.N.R₆ represents substituted or unsubstituted pyridonyl, favourably unsubstituted pyridonyl.

A favoured pyridonyl group is a 2-pyridon-1-yl group.
A favoured pyridonyl group is a 4-pyridon-1-yl group.

Suitably, when the moiety R₇.N.R₆ comprises further nitrogen atoms, it comprises 1 further nitrogen atom. Suitably, R₇.N.R₆ represents substituted or unsubstituted pyrimidinonyl or thiopyrimidinonyl, favourably unsubstituted pyrimidinonyl or thiopyrimidinonyl, in particular pyrimidinonyl. A favoured pyrimidinonyl group is a 4(1H)-pyrimidinon-1-yl a 6(1H)-pyrimidinon-1-yl or a 2(1H)-pyrimidinon-1-yl group.

A preferred substituent for the group R₇.N.R₆, and especially for the pyridonyl group, or the thiopyridonyl group is an alkyl group, suitably a C₁₋₆ alkyl group, such as a methyl group.

When R₅ represents a moiety (a) in which A is >C=NR₈, R₈ is preferably cyano.

When R₆ represents —NH.R₁₀, R₁₀ is suitably hydrogen, methyl, —CH—CH—CH₂, CH₂—C≡CH or cyclopropyl, preferably methyl, and R₇ is hydrogen.

When R₇ and R₁₀ together represent C₂₋₄ polymethylene, they favourably represent —CH₂CH₂—.

When moiety (b), represented by R₅, represents a substituted or unsubstituted aryl group, suitable aryl groups include monocyclic or bicyclic aryl groups which, in addition to the hydroxy group in the 2-position, can optionally contain one or more additional substitutents selected from halogen, cyano and lower alkyl.

When moiety (b) represented by R₅ represents an optionally substituted N- heteroaryl group, suitable N-heteroaryl groups include monocyclic or bicyclic N-heteroaryl groups which contains one or more nitrogen atoms and which, in addition to the hydroxy or N-oxide group in the 2-position, can optionally contain one or more additional substituents selected from halogen, amino, hydroxy, benzyloxy, phenyl, (lower alkyl)-phenyl, lower alkyl, lower alkoxy and lower alkoxycarbonyl.

In one particular aspect the present invention provides a compound falling wholly within the scope of formula (I) in which R₅ represents a moiety of formula (a), or where appropriate, a pharmaceutically acceptable salt thereof, or a pharmaceutically acceptable solvate thereof wherein:

A represents >C=X, wherein X represents O or S, or A represents a bond;

one of A₁ or A₂ represents hydrogen the other represents a group CF₃—Y—, wherein Y represents —CF₂—, >C=O or —CH(OH)—;

R₁ and R₂ independently represent hydrogen or C₁₋₆ alkyl; or R₁ and R₂ together represent a C₂₋₇ polymethylene moiety;

R₃ represents hydrogen, hydroxy, C₁₋₆ alkoxy or C₁₋₇ acyloxy and R₄ is hydrogen or R₃ and R₄ together represent a bond;

when A represents >C=X, then R₆ is hydrogen; C₁₋₆ alkyl optionally substituted by halogen, hydroxy, C₁₋₆ alkoxy, C₁₋₆ alkoxycarbonyl, carboxy or amino optionally substituted by one or two independent C₁₋₆ alkyl groups; or C₂₋₆ alkenyl; amino optionally substituted by a C₁₋₆ alkyl or C₂₋₆ alkenyl group or by a C₁₋₆ alkanoyl group optionally substituted by up to three halo atoms, by a phenyl group optionally substituted by C₁₋₆ alkyl, C₁₋₆ alkoxy or halogen; or aryl or heteroaryl, either being optionally substituted by one or more groups or atoms selected from the class of C₁₋₆ alkyl, C₁₋₆ alkoxy, hydroxy, halogen, trifluoromethyl, nitro, cyano, C₁₋₁₂ carboxylic acyl, or amino or aminocarbonyl optionally substituted by one or two C₁₋₆ alkyl groups; and R₇ represents hydrogen or C₁₋₆ alkyl;

or $R_6$ and $R_7$ together represent $-CH_2-(CH_2)_q-Z-(CH_2)_r-$ wherein q and r are 0 to 2 such that q+r is 1 or 2 and Z is $CH_2$, O, S or NR wherein R is hydrogen, $C_{1-9}$ alkyl, $C_{2-7}$ alkanoyl, phenyl $C_{1-4}$- alkyl, naphthylcarbonyl, phenylcarbonyl or benzylcarbonyl optionally substituted in the phenyl or naphthyl ring by one or two of $C_{1-6}$ alkyl, $C_{1-6}$ alkoxy or halogen; or R is mono- or bi-cyclic- heteroarylcarbonyl; when A represents a bond, then $R_6$ and $R_7$ together with the nitrogen atom to which they are attached, form a substituted or unsubstituted pyridonyl group or a substituted or unsubstituted thiopyridonyl group.

Preferably, when A represents >C=X then X is oxygen.

Preferably, $R_1$ and $R_2$ are both $C_{1-6}$ alkyl, and in particular $R_1$ and $R_2$ are both methyl.

When $R_3$ is alkoxy and $R_4$ is hydrogen, preferred examples of $R_3$ include methoxy and ethoxy, of which methoxy is more preferred. When $R_3$ is acyloxy and $R_4$ is hydrogen, a preferred class of $R_3$ is unsubstituted carboxylic acyloxy, such as unsubstituted aliphatic acyloxy. However, it is more preferred that $R_3$ and $R_4$ together are a bond, or that $R_3$ and $R_4$ are both hydrogen, or in particular, that $R_3$ is hydroxy and $R_4$ is hydrogen.

When $R_6$ represents alkyl, suitable alkyl groups include methyl, ethyl and n- and iso-propyl. Preferably $R_6$ is methyl.

A suitable halogen substituent for any alkyl represented by $R_6$, is a chloro or bromo substituent; favoured examples include methyl, ethyl or propyl, especially n-propyl, terminally substituted by chloro or bromo, especially chloro.

When $R_6$ represents alkyl substituted by hydroxy, favoured examples include methyl or ethyl terminally substituted by hydroxy.

When $R_6$ represents alkyl substituted by alkoxy, a suitable alkoxy group is a methoxy or ethoxy group; favoured examples include methyl or ethyl terminally substituted by methoxy or ethoxy.

When $R_6$ represents alkyl substituted by alkoxycarbonyl, a suitable alkoxycarbonyl group is a methoxycarbonyl or ethoxycarbonyl group; examples include methyl or ethyl terminally substituted by methoxycarbonyl or ethoxycarbonyl.

When $R_6$ represents alkyl substituted by carboxy, favoured examples include methyl or ethyl terminally substituted by carboxy.

When $R_6$ represents alkyl substituted by amino wherein the amino group is optionally substituted by one or two independent alkyl groups, favoured values include a group $(CH_2)_s R_t R_u$ where s is 1 to 6, and $R_t$ and $R_u$ are each independently hydrogen or alkyl. Suitable values for s include 1 and 2, in particular 1.

Preferably $R_t$ and $R_u$ are each independently selected from hydrogen and methyl.

When $R_6$ represents alkenyl, suitable values include vinyl, prop-1-enyl, prop-2-enyl, 1-methylvinyl, but-1-enyl, but-2-enyl, but-3-enyl, 1-methylenepropyl, or 1-methylprop-2-enyl, in both their E and Z forms where stereoisomerism exists.

When $R_6$ represents optionally substituted amino, suitable optional substituents for the amino group include a methyl; ethyl; propyl; butyl; allyl or a trichloroacetyl group; or a phenyl group optionally substituted by one methyl, methoxy group or one chloro atom, and in particular a phenyl group optionally substituted with amino, methylamino or phenylamino; the phenyl group in the phenylamino substituent being optionally substituted in the phenyl ring by one methyl or methoxy group or one chloro atom.

When $R_6$ represents aryl, favoured examples include phenyl and naphthyl, preferably phenyl.

When $R_6$ represents heteroaryl, suitable heteroaryl groups include 5- or 6-membered monocyclic or 9- or 10-membered bicyclic heteroaryl groups, preferably 5- or 6-membered monocyclic heteroaryl groups.

Preferred 5- or 6-membered monocyclic or 9- or 10-membered bicyclic heteroaryl groups are those containing one, two or three heteroatoms selected from the class of oxygen, nitrogen and sulphur and which, in the case of there being more than one heteroatom, are the same or different.

Suitable 5- or 6-membered monocyclic heteroaryl moieties include furyl, thienyl, pyrrolyl, oxazolyl, thiazolyl, imidazolyl and thiadiazolyl, and pyridyl, pyridazyl, pyrimidyl, pyrazyl and triazyl. Preferred 5- or 6- membered heteroaryl groups include furyl, thienyl, pyrrolyl and pyridyl, in particular 2- and 3-furyl, 2- and 3-pyrrolyl 2- and 3-thienyl, and 2-, 3- and 4-pyridyl.

Suitable 9- or 10-membered bicyclic heteroaryl moieties include benzofuryl, benzothienyl, indolyl and indazolyl, quinolinyl and isoquinolinyl, and quinazolinyl. Preferred 9- or 10- membered bicyclic heteroaryl groups include 2- and 3-benzofuryl, 2- and 3-benzothienyl, and 2- and 3-indolyl, and 2- and 3-quinolinyl.

Suitable substituents for any aryl or heteroaryl group represented by $R_6$ include one or more groups or atoms selected from alkyl, alkoxy, hydroxy, halogen, fluoroalkyl, nitro, cyano, carboxy or an ester thereof, alkylcarbonyloxy, amino, monoalkylamino, dialkylamino, aminocarbonyl, monoalkylaminocarbonyl or dialkylaminocarbonyl.

In any optionally substituted aryl or optionally substituted heteroaryl group, the preferred number of substituents is 1, 2, 3 or 4.

Preferred substituents for any substituted aryl or heteroaryl group include methyl, methoxy, hydroxy, chloro, fluoro, nitro or cyano.

One preferred sub-group of values for $R_6$ is that wherein $R_6$ represents phenyl or naphthyl or a 5- or 6-membered monocyclic or a 9- or 10-membered bicyclic heteroaryl, the phenyl, naphthyl or heteroaryl group being optionally substituted by one, two, three or four groups or atoms selected from the class of $C_{1-6}$ alkyl, $C_{1-6}$ alkoxy, halogen, trifluoromethyl, nitro or cyano.

When $R_6$ represents optionally substituted phenyl, preferred values include phenyl, 4-substituted phenyl, 3-substituted phenyl, 3,4-disubstituted phenyl and 3, 4, 5-trisubstituted phenyl, for example $R_6$ may suitably represent 4-fluorophenyl.

When $R_6$ represents an optionally substituted 5- or 6-membered monocyclic heteroaryl or an optionally substituted 9- or 10-membered bicyclic heteroaryl group, preferred values include unsubstituted 5- or 6-membered monocyclic heteroaryl or mono-substituted 5- or 6-membered monocyclic heteroaryl or 9- or 10-membered bicyclic heteroaryl, in particular unsubstituted 5- or 6-membered monocyclic heteroaryl or 9- or 10-membered bicyclic heteroaryl.

Preferably, when $R_6$ and $R_7$ together represent a linking chain $-A_3-A_4-$, $A_3$ represents a substituted or unsubstituted methylene group and $A_4$ represents a $-CH_2CH_2-$ or $-CH_2CH_2CH_2-$ group, for example $-CH_2CH_2CH_2-$.

When $A^1$ represents a substituted methylene group it is preferably substituted by an alkyl group especially a methyl group.

Preferably, when $R_6$ and $R_7$ together represent the moiety $-CH_2-(CH_2)_q-Z-(CH_2)_r-$ as hereinbefore defined, the moiety $R_6.N.CX.R_7$ represents either pyrrolidonyl or piperidonyl, preferably piperidonyl.

When Z is other than $CH_2$, q is often 0 or 1 and r is often 0 or 1.

Favoured examples of R and Z is NR include hydrogen, methyl, ethyl, n- and iso-propyl, n-, sec- and tert-butyl, benzyl, phenylcarbonyl or benzylcarbonyl optionally substituted in the phenyl ring by methyl, methoxy, chloro or bromo; furylcarbonyl, thienylcarbonyl, pyrrolylcarbonyl or indolylcarbonyl.

Preferably R is hydrogen, methyl, n-butyl, acetyl, benzyl, benzylcarbonyl, phenylcarbonyl or furylcarbonyl.

Most preferably R is methyl.

When used herein the term "halogen" refers to fluorine, chlorine, bromine and iodine; preferably chlorine.

Suitably alkyl groups, or alkyl groups forming part of other groups such as in the alkoxy group, are $C_{1-12}$ alkyl groups especially $C_{1-6}$ alkyl groups e.g. methyl, ethyl, n-propyl, iso-propyl, n-butyl, isobutyl or tert-butyl groups.

Suitably alkenyl groups are $C_{2-12}$ groups especially $C_{2-6}$ alkenyl groups.

Suitable alkynyl groups are $C_{2-12}$ alkynyl groups especially $C_{2-6}$ alkynyl groups.

Suitable acyloxy groups include alkylcarbonyloxy groups wherein the alkyl group is as defined above.

When used herein the term "fluoroalkyl" includes alkyl groups as defined above when substituted by one or more fluorine atoms, particular examples being trifluoromethyl and pentafluoroethyl.

When used herein the term 'aryl' includes phenyl and naphthyl optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl alkylcarbonyloxy, or alkylcarbonyl groups.

Suitable pharmaceutically acceptable salts of the compounds of formula (I) include acid addition salts and salts of carboxy groups.

Examples of pharmaceutically acceptable acid addition salts of the compounds of formula (I) includes acid addition salts of optionally substituted amino groups, such as the hydrochloride and hydrobromide salts. Such a salifiable group may form part of an $R_5$ group.

Examples of pharmaceutically acceptable salts of carboxy groups include metal salts, such as alkali metal salts, or optionally substituted ammonium salts.

The compounds of formula (I) may also exist in the form of solvates, preferably hydrates, and the invention extends to such solvates.

The compounds of formula (I), may exist in the form of optical isomers. For example chirality is present in those compounds of formula (I) wherein $R_3$ is hydrogen, hydroxy, alkoxy or acyloxy and $R_4$ is hydrogen, wherein $R_1$ and $R_2$ are different or wherein $R_6$ and $R_7$ together represent a linking group $—A_3—A_4—$, the said linking group possessing up to 4 chiral carbon atoms. The present invention extends to all optical isomers of the compounds of formula (I) whether in the form of single isomers or of mixtures thereof, such as racemates.

When $R_3$ is hydroxy, alkoxy or acyloxy and $R_4$ is hydrogen one isomer is that having the sterochemistry 4S, 3R, another is that having the stereochemistry 4R, 3S.

The compounds of formula (I) may also exist in geometrical isomeric forms all of which are encompassed by the present invention, including those wherein $R_5$ and $R_3$ are disposed either mutually trans with respect to one another or mutually cis with respect to one another, preferably mutually trans with respect to one another.

Particular examples of compounds of formula (I) include the compounds prepared in the Examples hereinafter.

The present invention also provides a process for the preparation of a compound of formula (I) or, where appropriate a pharmaceutically acceptable salt thereof, or a pharmaceutically acceptable solvate thereof which comprises;

i) for compounds of formula (I) wherein $R_5$ represents a moiety (a) and wherein A represents >C=X wherein X is O or S, acylating a compound of formula (II):

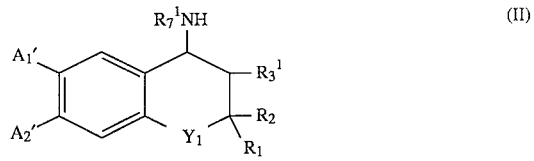

wherein, $R_1$, $R_2$ and $Y_1$ are as defined hereinbefore, $A_1'$ represents $A_1$ as defined above or a protected form thereof and $A_2'$ represents $A_2$ as defined above or a protected form thereof, $R_3^1$ is hydroxy, alkoxy or acyloxy, and $R_7^1$ is hydrogen or alkyl, a) with an acylating agent of formula (III):

wherein $L_7$ is a leaving group, and $R_{14}$ is hydrogen, alkyl optionally substituted by halogen, hydroxy, alkoxy, alkoxycarbonyl, carboxy or amino optionally substituted as hereinbefore defined for $R_6$, alkenyl or optionally substituted aryl or heteroaryl as hereinbefore defined for $R_6$, or a group convertible to $R_6$ as hereinbefore defined, and thereafter, when $R^1_7$ is hydrogen and $R_{14}$ is $Y_2(CH_2)_z$, wherein z is 3 or 4 and $Y_2$ is a leaving group, cyclising the resultant compound;

b) with a compound of formula (IV)

wherein $R_{15}$ is hydrogen, alkyl, alkenyl, alkanoyl optionally substituted by up to three halo atoms, or phenyl optionally substituted by alkyl, alkoxy or halogen; and X is oxygen or sulphur, and thereafter when $R_{15}$ is hydrogen, optionally converting $R_{15}$; or ii) for compounds of formula (I) wherein $R_5$ represents a moiety (a) and wherein A represents >C=X wherein X is O or S, and $R_7$ and $R_8$ together represent a linking chain $—A_3—A_4—$ as defined above in relation to formula (I), reacting a compound of formula (V):

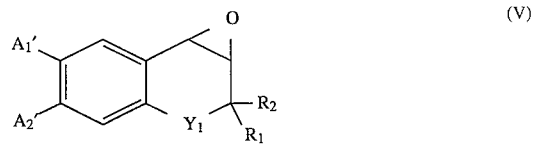

wherein $A_1'$, $A_2'$, $R_1$, $R_2$ and $Y_1$ are as hereinbefore defined, with an activated form of a compound of formula (VI):

wherein $R_{16}$ and $R_{17}$ together represent a linking chain of formula $—A_3—A_4—$;

iii) for compounds of formula (I) wherein $R_5$ represents a moiety (a) and wherein A represents a bond and $R_6$ and $R_7$ together with the nitrogen to which they are attached form an unsaturated heterocyclic ring having 5 to 7 ring atoms, which ring atoms comprise up to 2 further nitrogen atoms and a carbon atom, the carbon atom being substituted with either an oxo group or a thioxo group, the remaining ring atoms being substituted or unsubstituted, by reacting a compound of the above-defined formula (V) with an activated form of a compound of formula (VIA):

$$R_7^2 NHR_6^1 \quad (VIA)$$

wherein $R_6^1$ and $R_7^2$ together with the nitrogen to which they are attached form the said heterocyclic ring;

(iv) for compounds of formula (I) wherein $R_5$ represents a moiety of formula (a) in which A is >C=X and X is $NR_8$, either:

a) for compounds wherein $R_{10}$ is other than hydrogen and $R_8$ is CN or $SO_2NH_2$, by reacting a compound of formula (VII):

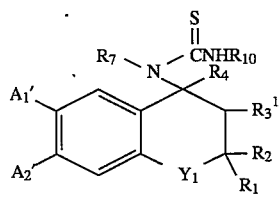

(VII)

wherein $R_1$, $R_2$, $R_4$, $R_7$ and $Y_1$ are as defined in relation to formula (I) and $A_1'$, $A_2'$ and $R_3^1$ are as defined in relation to formula (II), with phosgene ($COCl_2$) and either cyanamide (for compounds wherein $R_8$ is CN) or sulphamide (for compounds wherein $R_8$ is $SO_2NH_2$); or b) for compounds wherein $R_7$ and $R_{10}$ together are $C_{2-4}$ polymethylene, by reacting dimethyl N-cyanodithio-iminocarbonate with a compound of formula (VIII):

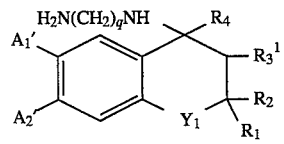

(VIII)

wherein q is 2, 3 or 4 and the remaining variables are as hereinbefore defined; or v) for compounds of formula (I) wherein $R_5$ represents a moiety of formula (b), either:

a) for compounds wherein $T_1$ in moiety (b) represents >C—OH, by deprotecting a compound of formula (IX):

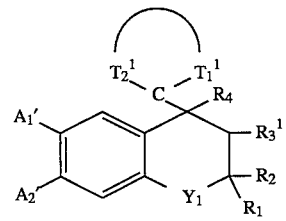

(XI)

wherein $R_1$, $R_2$, $R_4$ and $Y_1$ are as defined in relation to formula (I), $A_1'$, $A_2'$ and $R_3^1$ are as defined in relation to formula (II), $T_1^1$ represents >C—$OT_4$ wherein $T_4$ is a hydroxyl protecting group and $T_2^1$ together with $CT_1^1$ represents an optionally substituted aryl group; or b) for compounds wherein $R_1$ in moiety (b) represents $N(O)_n$, by oxidising a compound of formula (X):

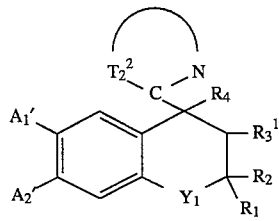

(X)

wherein $R_1$, $R_2$, $R_3^1$, $R_4$, $A_1'$, $A_2'$ and $Y_1$ are as defined above and $T_2^2$ together with C—N represents an optionally substituted or N-heteroaryl group; or vi) for compounds of formula (I) wherein $R_5$ represents a moiety of formula (c), by reacting a compound of the abovedefined formula (V), with a compound of formula (XI):

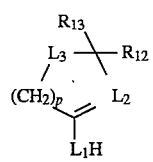

(XI)

wherein $L_1$, $L_2$, $L_3$, $R_{12}$, $R_{13}$ and p are as defined in relation to moiety (c) of formula (I);

and thereafter if required, carrying out one or more of the following optional steps:

(a) converting $A_1'$ to $A_1$ and/or converting $A_2'$ to $A_2$;

(b) converting a compound of formula (I) into a further compound of formula (I);

(c) forming a pharmaceutically acceptable salt of the compound of formula (I);

(d) forming a pharmaceutically acceptable solvate of the compound of formula (I) or a pharmaceutically acceptable salt thereof.

In the process variant i) a) acylation of a compound of formula (II) with an acylating agent of formula (III), the leaving group $L_7$ is a group that is displaceable by a primary or secondary amino nucleophile. Examples of such a group include $C_{1-4}$ alkanoyloxy, and halogen, such as chloro and bromo. When the leaving group $L_1$ is either of these examples, the acylating agent of formula (III) is either an acid anhydride or an acid halide. When it is an acid anhydride, it may be a mixed or simple anhydride. If it is a mixed anhydride, it may be prepared in situ from a carboxyliic acid and an acid halide, although this is less preferred than using the halide itself.

In process variant i) a), when $R_6$ in the desired compound of formula (I) is an $R_6$ optionally substituted amino-substituted alkyl group as hereinbefore defined, it is preferred that $R_{14}$ is a group convertible to the $R_6$ substituted alkyl group as hereinbefore defined, in particular that it is alkyl substituted by halo, especially bromo. The $R_{14}$ halo substituent in the resultant compound of process variant i) a) may be converted to an $R_6$ substituent which is amino optionally substituted as hereinbefore defined by a conventional amination reaction with ammonia or a corresponding alkyl- or dialkylamine.

Less favourably $R_{14}$ may be alkyl substituted by protected amino, protected alkylamino or amino substituted by two independent alkyl groups, it being necessary to protect the $R_9$ amino function in process variant i) a).

When the acylating agent of formula (III) is an acid anhydride, the acylation of the compound of formula (II)

may be carried out in the presence of an acid acceptor, such as sodium acetate, optionally using the anhydride as the solvent.

When the acylating agent of formula (III) is an acid halide, the acylation of the compound of formula (II) is, preferably, carried out in a non-aqueous medium, such as dichloromethane, in the presence of an acid acceptor, such as triethylamine, trimethylamine, pyridine, picoline or calcium, potassium or sodium carbonate.

When the compound of formula (II) comprises a hydroxy group, for example when $R_3^1$ is hydroxy, there is a risk of a side-reaction between the hydroxy group and the acylating agent of formula (III). However, the reaction may be carried out under controlled conditions such that only the amine, $R_7^1$NH-is acylated, for example, by using a $C_{2-9}$ acyloxy group as the leaving group $L_7$, in the acylating agent of formula (III) in the manner as previously described for an acid anhydride, and/or effecting the reaction at relatively low temperature, e.g. at below 10° C.

Alternatively $R_3^1$ may be $C_{1-7}$ acyloxy in a compound of formula (II), although less preferably if $R_3$ in the resultant compound of formula (I) is to be hydroxy, and, after reaction with the acylating agent of formula (III), be converted into hydroxy, as described hereinafter.

When $R_{14}$ is $Y_2(CH_2)_z$ where the variables are as hereinbefore defined, the leaving group $Y_2$ is a group that is displaceable by a secondary amino nucleophile adjacent to a carbonyl function. A preferred example is chloro.

The cyclisation reaction when $R_{14}$ is $Y_2(CH_2)_z$ where the variables are as hereinbefore defined is preferably carried out in an inert solvent such as dimethylformamide.

In process variant i) b), when $R_{15}$ in a compound of formula (IV) is alkyl, alkanoyl optionally substituted as hereinbefore defined, or phenyl optionally substituted as hereinbefore defined, the reaction between the compounds of formulae (II) and (IV) is, preferably, carried out in a solvent, such as dichloromethane, at below room temperature, in particular below 10° C.

When $R_{15}$ is hydrogen, the reaction between the compounds of formulae (II) and (IV) is, preferably, carried out using a corresponding alkali metal cyanate or thiocyanate, for example that of sodium or potassium, in an optionally methanolic aqueous medium acidified with a mineral acid, such as dilute hydrochloride acid. A slightly elevated temperature such as 50° to 90° C. is apt.

In process variant ii), a suitable activated form of a compound of formula (VI) is an ionic form. Thus in the reaction between a compound of formula (V) and a compound of formula (VI), it is preferred that the reaction is carried out under basic conditions so as to facilitate the formation of the anion of the compound of formula (VI), for example, in the presence of an alkali metal base such as potassium t-butoxide or sodium hydride.

The reaction between the compounds of formula (V) and (VI) may be carried out in any suitable aprotic solvent at a temperature that provides a convenient rate of formation of the compound of formula (I), such as at ambient temperature or at an elevated temperature, for example 40° C.

Conveniently, the compound of formula (VI) may itself be used as the solvent for the reaction between compounds of formulae (V) and (VI).

In process variant iii), a suitable activated form of a compound of formula (VIA) is an ionic form. Thus in the reaction between a compound of formula (V) and a compound of formula (VIA), it is preferred that the reaction is carried out under basic conditions so as to facilitate the formation of the anion of the compound of formula (VIA), for example, in the presence of an alkali metal base such as potassium t-butoxide or sodium hydride.

The reaction between the compounds of formulae (V) and (VIA) may be carried out in any suitable aprotic solvent, for example dimethylsulphoxide, at a temperature that provides a convenient rate of formation of the compound of formula (I), such as at ambient temperature or at an elevated temperature, but conveniently at ambient temperature.

In process variant iva), the reaction is preferably carried out in an inert solvent, such as tetrahydrofuran, at −10° to +25° C., preferably around 0° C. to ambient, in an inert atmosphere, for example, under nitrogen, preferably in the presence of a base, such as diisopropylethylamine.

Alternative methods of forming compounds of formula (I) wherein $R_5$ represents a moiety of formula (a) in which A is >C=X and X is $NR_8$ are as described in J.Med.Chem. 1978 Vol 21 p773–781.

Intermediates of formula (VII) may be prepared according to analogous procedures disclosed in EP-A-107423, EP-A-168619, EP-A-126367, EP-A-205292 and EP-A-321175 or in European Patent Application Number 89309272.6.

In process variant ivb), the reaction suitably takes place at elevated temperatures, preferably at reflux temperatures, in an inert solvent, such as toluene.

The reaction conditions for proces variant v) are generally equivalent to those described in European Application, Publication Number 298452.

The intermediate compounds of formula (IX) may conveniently be prepared using analogous procedures to those described in EP 298452.

In process variant vi), the reaction is suitably effected by using an anionic form of compound (XI) formed in situ by using a strong base, for example sodium hydride.

In process variant vi) the reaction conveniently takes place in an inert solvent, for example in dimethylformamide, dimethyl sulphoxide, tetrahydrofuran, dimethylpropyleneurea or mixtures thereof, at low, medium or high temperatures, preferably at room temperature, for example at about 20° to 25° C. It is often convenient to catalyse the reaction, for example using catalytic or stoichiometric quantities of copper(I)bromide, magnesium bromide or titanium alkoxides, or to catalyse the epoxide opening with catalytic or stochiometric quantities of a Lewis acid such as $BF_3.OEt_2$.

The compounds of formula (XI) may suitably be prepared using analogous procedures to those described in European Application, Publication Number 107423 or United Kingdom Application, Publication Number 2204868.

Suitable conversions of a compound of formula (I) to a further compound of formula (I) include:

(i) converting $R_3$ in the resulting compound of formula (I) into another $R_3$;

(ii) converting a compound of formula (I) wherein $R_3$ and $R_4$ represent hydroxy and hydrogen respectively to give another compound of formula (I), wherein $R_3$ and $R_4$ together represent a bond;

(iii) reducing any compound of formula (I) wherein $R_3$ and $R_4$ together represent a bond; to give another compound of formula (I), wherein $R_3$ and $R_4$ each represent hydrogen;

(iv) thiating a compound of formula (I) to convert any —CO— group in the moiety of formula $R_7.N.A.R_6$ into a —CS— group;

(v) when $R_3$ is other than hydrogen, interconverting the cis and trans mutual configuration of the variables $R_3$ and $R_4$; or (vi) converting $A_1$ into another $A_1$ or $A_2$ into another $A_2$.

The reaction of the compounds of formulae (II) with (III) or (IV) results in a compound of formula (I) wherein $R_3$ is hydroxy, alkoxy or acyloxy, whereas the reaction of the compounds of formulae (V) and (VI) and (V) with (VIA) results in a compound of formula (I) wherein $R_3$ is hydroxy. Examples of an optional conversion of $R_3$ in a compound of formula (I) into another $R_3$ are generally known in the art. For example, when $R_3$ is hydroxy, it may be alkylated using an alkyl iodide in an inert solvent, such as toluene, in the presence of a base, such as sodium hydride or potassium hydroxide, or it may be acylated using a carboxylic acid chloride or an appropriate anhydride in a non-hydroxylic solvent, such as toluene or dichloromethane, in the presence of an acid acceptor such as triethylamine. When $R_3$ is alkoxy it may be converted into a hydroxy group by any conventional dealkylation method for example by treatment with trimethylsilyliodide in an aprotic solvent. In addition, when $R_3$ is acyloxy it may be converted into hydroxy by conventional hydrolysis using, for example, dilute mineral acid.

The optional conversion of a compound of formula (I), wherein $R_3$ and $R_4$ are hydroxy and hydrogen respectively, into another compound of formula (I), wherein $R_3$ and $R_4$ together are a bond, may be carried out by dehydration under conventional dehydration conditions, for example, by using a dehydrating agent, such as sodium hydride, in inert solvent, such as dry tetrahydrofuran, at reflux temperature; alternatively the hydroxy group represented by $R_3$ may be converted into a leaving group such as a mesyloxy or tosyloxy group and the resulting compound treated with a base such as sodium hydride to provide the compound of formula (I) wherein $R_3$ and $R_4$ together represent a bond.

The reduction of a compound of formula (I), wherein $R_3$ and $R_4$ together are a bond, into another compound of formula (I), wherein $R_3$ and $R_4$ are each hydrogen, may be carried out by hydrogenation using a catalyst of palladium on charcoal.

The thiation of the $R_7.N.A.R_6$ moiety in a compound of formula (I) to give another compound of formula (I), is, preferably, carried out with conventional thiation agents, such as hydrogen sulphide, phosphorus pentasulphide and Lawesson's reagent (p-methoxyphenylthiophosphine sulphide dimer). The use of hydrogen sulphide and phosphorus pentasulphide may lead to side-reactions and, therefore, the use of Lawesson's reagent is preferred. The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is, preferably, carried out under reflux in a dry solvent, such as toluene or methylene chloride.

The interconversion of the cis and trans configuration of the variables $R_3$ and $R_4$ is generally carried out by changing the configuration of variable $R_3$, especially when $R_3$ represents hydroxyl, by means of any convenient conventional procedure.

Suitable conversions of $A_1$ into another $A_1$ include the conversion of $CF_3CO-$ into $CF_3CH(OH)-$ and the conversion of $CF_3CO-$ into $CF_3CF_2-$ by using any suitable chemical procedure, including those described hereinafter.

The optional formation of a pharmaceutically acceptable salt, when the resulting compound of formula (I) contains a salifiable group, may be carried out conventionally. Similarly, pharmaceutically acceptable solvates, for example hydrates, may be prepared using any convenient conventional procedure.

A compound of formula (II) may be prepared by reacting a compound of formula (V), as defined hereinbefore, with a compound of formula (XII):

$$R_7{}^1NH_2 \qquad (XII)$$

wherein $R_7{}^1$ is as defined hereinbefore; and optionally converting $R_3{}^1$ hydroxyl in the resulting compound of formula (II) into another $R_3{}^1$.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (II) may be isolated from the reaction mixture by removal of the solvent, for example, by evaporation under reduced pressure. Any epoxide impurity may be removed conventionally, for example for chromatography.

The optional conversion of the hydroxy group for $R_3{}^1$ in the resulting compound of formula (II) into a alkoxy or acyloxy group may be carried out as described hereinbefore in relation to the corresponding conversion of $R_3$ in a compound of formula (I).

A compound of formula (V) may be prepared by reacting a compound of formula (XIII):

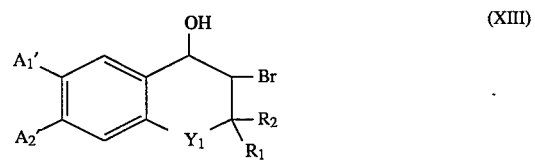

wherein $A_1'$, $A_2'$, $R_1$, $R_2$ and $Y_1$ are as hereinbefore defined, the bromine atom being trans to the hydroxy group, with a base, suitably an alkali metal base such as a potassium alkoxide, for example potassium t-butoxide, or potassium hydroxide, in a solvent, such as ether aqueous dioxan or dimethylsulphoxide.

In one preferred form of the process for preparing a compound of formula (I), a compound of formula (V) may be prepared in situ, preferably in anhydrous conditions, by reaction of a compound of formula (XIII) with a strong base, preferably an alkali metal alkoxide, for example potassium t-butoxide, and thereafter the said compound of formula (V) may be reacted in the abovedefined process ii), iii) or vi) to provide a compound of formula (I).

A compound of formula (XIII) may be prepared by reaction of a compound of formula (XIV):

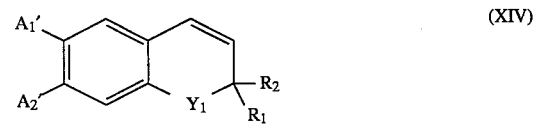

wherein $A_1'$, $A_2'$, $R_1$, $R_2$ and $Y_1$ are as defined hereinbefore, with N-bromosuccinimide in a solvent, such as aqueous dimethyl sulphoxide.

A compound of formula (V) may also be prepared from a compound of formula (XIV) by reaction with a peracid, preferably m-chloroperbenzoic acid, in an inert solvent such as dichloromethane at ambient temperature.

A compound of a formula (XIV) may be prepared by reacting a compound of formula (XV):

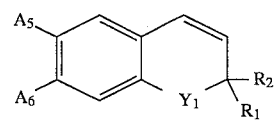

wherein $R_1$, $R_2$ and $Y_1$ are as defined in relation to formula (I) and wherein one of $A_5$ or $A_6$ represents a halogen atom, preferably bromine, and the other one of $A_5$ or $A_6$ represents a hydrogen atom, with a compound of formula (XVI):

$$CF_3CO.X \qquad (XVI)$$

wherein X represents a leaving group; and thereafter where required, converting any moiety of formula $CF_3CO-$ into a moiety $CF_3CH(OH)-$ or $CF_3CF_2-$, or where appropriate preparing a protected form of such groups.

A suitable leaving group X is a trifluoroacetyloxy group.

The reaction between the compounds of formulae (XV) and (XVI) may be carried out in any suitable aprotic solvent, such as tetrahydrofuran or dimethylformamide, at any temperature providing a convenient rate of formation of the required compound, such as at an elevated temperature, for example the reflux temperature of the solvent.

Preferably, the compound of formula (XV) is in an activated form, for example in the form of a magnesium Grignard salt prepared in conventional manner.

Alternatively, a compound of formula (XIV) may be prepared by reacting a compound of the hereinbefore defined formula (XV), with an alkali metal salt of pentafluoropropionic acid, suitably the sodium salt, and preferably in the presence of a copper (I) halide such as copper iodide.

The reaction between the compound of formula (XV) and the pentafluoropropionic acid salt is suitably carried out in an aprotic solvent such as dimethylformamide, suitably at an elevated temperature such as the reflux temperature of the solvent.

In an alternative aspect the present application also provides a process for the preparation of a compound of formula (I), or a pharmaceutically acceptable salt thereof, or a pharmaceutically acceptable solvate thereof, which comprises reacting a compound of formula (XVII):

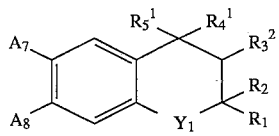

wherein $R_1$, $R_2$ and $Y_1$ are as defined in relation to formula (I), one of $A_7$ and $A_8$ represents hydrogen and the other represents a bromine atom, $R_3^2$ represents $R_3^1$ or $R_3^2$ together with $R_4^1$ represent a bond and $R_5^1$ represents $R_5$ as defined above or a protected form thereof, with either a) a compound of the abovedefined formula (XVI); or b) an alkali metal salt of pentafluoropropionic acid;

and thereafter if required, carrying out one or more of the following optional steps:

(a) converting $A_1'$ to $A_1$ and/or converting $A_2'$ to $A_2$;

(b) converting a compound of formula (I) into a further compound of formula (I);

(c) forming a pharmaceutically acceptable salt of the compound of formula (I);

(d) forming a pharmaceutically acceptable solvate of the compound of formula (I) or a pharmaceutically acceptable salt thereof.

The reaction conditions for the reaction between a compound of formula (XVII) with either a compound of formula (XVI) or an alkali metal salt of pentafluoropropionic acid are analogous to those described above for the reaction between compounds of formulae (XV) and (XVI) or between (XV) and pentafluoropropionic acid alkali metal salts, respectively.

Preferably in compound (XVII), $R_3^2$ and $R_4^1$ together represent a bond.

Suitable protected forms $R_5^1$ are those used conventionally in the art.

Compounds of formula (XVII) may be prepared according to analogous procedures mentioned herein.

The conversion of any moiety $CF_3.CO-$ into $CF_3CH(OH)-$ may be carried out conventionally, for example by reduction using potassium borohydride in methanol at 0° C.

The conversion of any moiety $CF_3.CO-$ into $CF_3.CF_2-$ may be carried out conventionally, such as by using any convenient fluorinating agent, for example by using diethylaminosulphur trifluoride in a solvent such as dichloromethane at ambient temperature.

As mentioned previously, some of the compounds of formula (I) may exist in optically active forms, and the processes of the present invention produce mixtures of such forms. The individual enantiomers may be resolved by conventional methods. For example, a mixture of enantiomers of a compound of formula (I) may be derivatised with an optically active derivatising agent to provide a mixture of diastereoisomeric derivatives, which may then be separated using any convenient procedure, for example chromatography. A suitable derivatising agent is an optically active isocyanate, such as (−)-α-methylbenzylisocyanate, which provides the corresponding carbamate.

In an alternative aspect, the optically active forms of the compounds of formula (I) may be prepared using conventional stereospecific synthetic procedures starting from chiral substrates.

It is preferred that the compounds of formula (I) are isolated in substantially pure form.

The intermediates of formulae (II), (V), (VII), (VIII), (IX), (X), (XIII), (XIV) and (XVII) are believed to be novel and accordingly each forms part of the present invention.

The intermediates of formulae (III), (IV), (VI), (VIA), (XI), (XII), (XV) and (XVI) are known or may be prepared using conventional procedures, for example those disclosed hereinbefore or in Advanced Organic Chemistry, 3rd Edition, (1985), Published by John Wiley and Sons.

When used herein 'disorders associated with smooth muscle contraction of the gastro-intestinal tract, uterus or the urinary tract including the ureter', includes irritable bowel syndrome and diverticular disease; premature labour; incontinence; renal cholic and disorders associated with the passage of kidney stones.

When used herein 'cardiovascular disorders' includes disorders other than hypertension, such as congestive heart failure, angina, peripheral vascular disease.

When used herein "pulmonary hypertension" relates to arterial hypertension, capillary hypertension or venous-hypertension, especially arterial hypertension.

Also pulmonary arterial hypertension relates to both primary arterial hypertension and to pulmonary arterial hypertension occurring secondary to pulmonary diseases such as chronic bronchitis, emphysema, kyphoscoliosis and conditions such as chronic mountain sickness.

When used herein "right heart failure" relates to disorders such as cor pulmonale and congenital abnormalities of the heart. Cor pulmonale often occurs secondary to certain lung diseases such as chronic bronchitis and emphysema.

Congenital abnormalities of the heart include disorders, such as atrial septal defect, tetralogy of fallot, venticular septal defect and persistent ductus arteriosus.

The compounds of formula (I), the pharmaceutically acceptable salts thereof or the pharmaceutically acceptable solvates thereof, have been found to have bronchodilator activity and/or blood-pressure lowering activity. They are therefore useful in the treatment of respiratory tract disorders, such as reversible airways obstruction, diverticular disease and asthma and also hypertension. They may also be of potential use in the treatment of other disorders hereinbefore described.

The present invention accordingly provides a pharmaceutical composition which comprises an effective, non-toxic amount of a compound of formula (I), or a pharmaceutically acceptable salt thereof or a pharmaceutically acceptable solvate thereof, and a pharmaceutically acceptable carrier.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions of this invention, especially for the treatment of reversible airways obstruction and asthma, may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

In one further aspect of the present invention, there is provided a compound of the abovedefined formula (I) or, where appropriate, a pharmaceutically acceptable salt thereof, or a pharmaceutically acceptable solvate thereof, in the form of a microfine powder. As indicated such a powder is of particular value in administration via insufflation.

The present invention further provides a pharmaceutical composition, in particular a composition for inhaled administration, which comprises a compound of the abovedefined formula (I) or, where appropriate, a pharmaceutically acceptable salt thereof, or a pharmaceutically acceptable solvate thereof, in the form of a microfine powder and optionally a pharmaceutically acceptable carrier. Suitable carriers are those used conventionally in the art, for example lactose.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg ml$^{-1}$ of compound but more generally 0.1 to 10 mg ml$^{-1}$, for use with standard nebulisation equipment.

The present invention further provides a method for the treatment of respiratory tract disorders, such as reversible airways obstruction and, especially asthma, or hypertension in mammals including man, which method comprises administering an effective, non-toxic amount of a compound of formula (I), or a pharmaceutically acceptable salt thereof or a pharmaceutically acceptable solvate thereof to the mammal in need thereof.

The present invention also provides a method for the treatment of disorders associated with smooth muscle contraction of the gastro-intestinal tract, cardiovascular disorders and/or in the treatment and/or prophylaxis of disorders associated with pulmonary hypertension and disorders associated with right heart failure and/or in the treatment of epilepsy, in mammals including man, which method comprises administering an effective, non-toxic amount of a compound of formula (I), or a pharmaceutically acceptable salt thereof or a pharmaceutically acceptable solvate thereof to the mammal in need thereof.

An effective amount will depend on the relative efficacy of the compounds of the present invention, the severity of the disorder being treated and the weight of the sufferer. Suitably, a unit dose form of a composition of the invention may contain from 0.001 to 100 mg of a compound of the invention (0.001 to 10 mg via inhalation) and more usually from 0.01 to 50 mg, for example 0.05 to 25 or 0.5 to 25 mg such as 0.1, 1, 2, 5, 10, 15 or 20 mg. Such compositions may be administered from 1 to 6 times a day, more usually from 2 to 4 times a day, in a manner such that the daily dose is from 0.002 to 200 mg for a 70 kg human adult and more particularly from 0.005 to 100 mg. That is in the range of about $2.5.10^{-5}$ mg/kg/day to 3 mg/kg/day and more particularly in the range of about $5.10^{-5}$ mg/kg/day to 1.5 mg/kg/day.

The present invention also provides a compound of formula (I) or a pharmaceutically acceptable salt thereof, or a pharmaceutically acceptable solvate thereof, for use as an active therapeutic substance.

In particular, the present invention provides a compound of formula (I) or a pharmaceutically acceptable salt thereof, or a pharmaceutically acceptable solvate thereof, for use in the treatment of respiratory tract disorders or hypertension or disorders associated with smooth muscle contraction of the gastro intestinal tract or cardiovascular disorders and/or in the treatment and/or prophylaxis of disorders associated with pulmonary hypertension and disorders associated with right heart failure and/or in the treatment of epilepsy.

Also the present invention provides the use of a compound of formula (I), or a pharmaceutically acceptable salt thereof, or a pharmaceutically acceptable solvate thereof for the manufacture of a medicament for the treatment of respiratory tract disorders or hypertension or disorders associated with smooth muscle contraction of the gastro intestinal tract or cardiovascular disorders and/or in the treatment and/or prophylaxis of disorders associated with pulmonary hypertension and disorders associated with right heart failure and/or in the treatment of epilepsy.

The following Procedures relate to the preparation of intermediates and the following Examples relate to the preparation of compounds of formula (I).

PROCEDURE 1

2,2-Dimethyl-6-trifluoroacetyl-2H-1-benzopyran

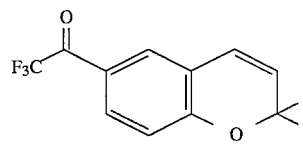

A mixture of 6-bromo-2,2-dimethyl-2H-1-benzopyran (4.0 g, 16.5 mmol) and magnesium turnings (0.44 g, 18.3 mmol) in tetrahydrofuran (35 ml) was heated at 50° C. with iodine (10 mg) until all the magnesium had been consumed. The solution was cooled to 0° C. and trifluoroacetic anhydride (4.8 ml, 34.3 mmol) added dropwise over 0.5 h and stirring continued for a further 16 hr. Hydrochloric acid (60 ml, 2M) was added and the mixture extracted with ether (3×60 ml). The organics were separated, dried (MgSO$_4$) and concentrated under reduced pressure to a brown liquid which was chromatographed on silica. Elution with (2:1. hexane/CHCl$_3$) yielded 2,2-dimethyl-6-trifluoroacetyl- 2H-1-benzopyran (2.97g, 69%) as a yellow liquid.

$^1$H NMR (CDCl$_3$) δ: 1.5 (s, 6H); 5.75 (d, J=10Hz, 1H); 6.4 (d, J=10Hz, 1H); 6.9 (d, J=8Hz, 1H); 7.75 (br.s, 1H); 7.95 (br. d, J=8Hz, 1H).

Mass Spectrum: Observed mass 256.0711 Theoretical mass 256.0711

PROCEDURE 2

2,2-Dimethyl-6-pentafluoroethyl-2H-1-benzopyran

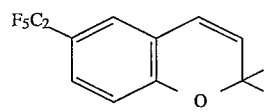

A solution of 2,2-dimethyl-6-trifluoroacetyl-2H-1-benzopyran (1.02 g, 3.98 mmol) and diethylaminosulphur trifluoride (DAST), (0.85 ml, 6.34 mmol) in dichloromethane (20 ml) was stirred for 16 h. The solution was poured into water (20 ml) and extracted with CH$_2$Cl$_2$ (3×20 ml), the organics were separated, dried (MgSO$_4$) and concentrated to a yellow liquid which was chromatographed on silica. Elution with hexane yielded 2,2-dimethyl-6-pentafluoroethyl-2H-1-benzopyran (0.93 g, 84%) as a colourless liquid.

$^1$H NMR (CDCl$_3$) δ: 1.45 (s, 6H): 5.65 (d, J=10Hz, 1H); 6.3 (d, J=10Hz, 1H); 6.85 (d, J=8Hz, 1H); 7.15 (d, J=2Hz, 1H); 7.3 (d.d., J=8, 2Hz, 1H).

Mass spectrum: Observed mass 278.0737 Theoretical mass 278.0730

PROCEDURE 3

Trans-3-bromo-3,4-dihydro-2,2-dimethyl-6-pentafluoroethyl- 2H-1-benzopyran-4-ol

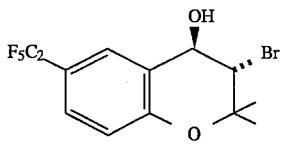

To a solution of 2,2-dimethyl-6-pentafluoroethyl-2H-1-benzopyran (0.419 g, 1.51 mmol) in dimethylsulphoxide (DMSO, 5 ml) containing 5 drops of water was added N-bromosuccinimide (0.56 g, 3.15 mmol). The solution was stirred for 4 h and then poured into water (30 ml). The mixture was extracted with ethyl acetate (50 ml) and the organics washed with water (4×30 ml), dried (MgSO$_4$) and evaporated in vacuo to a white solid (0.50 g, 88%). An analytical sample of trans-3- bromo-3,4-dihydro-2,2-dimethyl- 6-pentafluoroethyl-2H-1-benzopyran-4-ol, m.p. 86° C., was obtained after preparative layer chromatography on silica (eluent ethyl acetate/hexane, 1:1).

$^1$H NMR (CDCl$_3$) δ: 1.45 (s, 3H); 1.65 (s, 3H); 2.7 (d, J=4Hz, 1H); 4.15 (d, J=9Hz, 1H); 4.95 (dd, J=9, 4Hz, 1H); 6.9 (d, J=9Hz, 1H); 7.4 (dd, J=9, 2Hz, 1H), 7.75 (d, J=2Hz, 1H).

Analysis: Found C, 41.71; H, 3.35 C$_{13}$H$_{12}$BrF$_5$O$_2$ requires C, 41.62; H, 3.23%.

PROCEDURE 4

Trans-3-bromo-3,4-dihydro-2,2-dimethyl-6-trifluoroacetyl-2H-1-benzopyran-3-ol

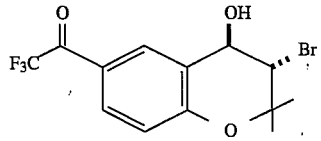

To a solution of 2,2-dimethyl-6-trifluoroacetyl-2H-1-benzopyran (0.33 g, 1.29 mmol) in DMSO (5 ml) containing 5 drops of water was added N-bromosuccinimide (0.48 g, 2.70 mmol). The solution was stirred for 1 h, diluted with ether (60 ml), washed with brine (4×50ml), dried (MgSO$_4$) and concentrated in vacuo to an off-white solid. Chromatography on silica (2:1 hexane/ether) yielded trans-3-bromo-3,4, dihydro-2,2-dimethyl-6-trifluoroacetyl- 2H-1-benzopyran-3-ol (0.31 g, 68%), m.p. 97°-98° C. (hexane/ether).

$^1$H NMR (CDCl$_3$) δ: 1.45 (s, 3H); 1.65 (s, 3H); 2.9 (br, 1H); 4.1 (d, J=9Hz, 1H); 4.95 (d, J=9Hz, 1H); 6.95 (d, J=9Hz, 1H); 7.95 (dd, J=9, 1Hz, 1H); 8.25 (d, J=1Hz, 1H).

Analysis: found: C, 44.46; H, 3.39; C$_{13}$H$_{12}$BrF$_3$O$_3$ requires: C, 44.21; H, 3.43%.

PROCEDURE 5

Trans-3-bromo-3,4-dihydro-2,2-dimethyl-6-(1-hydroxy-2, 2,2-trifluoroethyl)-2H-1-benzopyran-3-ol

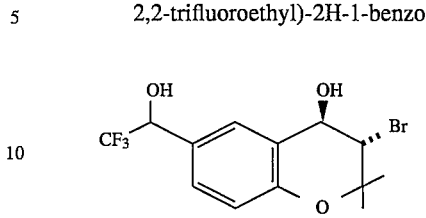

Potassium borohydride (0.089 g, 1.65 mmol) was added portionwise to a solution of trans-3-bromo-3,4-dihydro-2,2-dimethyl-6-trifluoroacetyl-2H-1-benzopyran- 3-ol (0.53 g, 1.50 mmol) in methanol (10 ml) at 0° C., and the solution stirred for 3 h. The mixture was concentrated and the residues partitioned between ethyl acetate and water. The organics were dried (MgSO$_4$), concentrated and the resulting oil purified by p.l.c. (3:2 hexane/ethyl acetate) to yield trans-3-bromo-3, 4-dihydro -2,2-dimethyl-6-(1-hydroxy-2, 2,2-trifluoroethyl)- 2H-1-benzopyran-3-ol (0.37 g, 69%) as a 1:1 mixture of diastereoisomers, m.p. 132°–134° C.

$^1$H NMR (CDCl$_3$) δ: 1.4 (s, 3H); 1.6 (s, 3H); 2.75 (m, 2H); [4.1 (d, J=7Hz) and 4.15 (d, J=8Hz), total 1H]; 4.9 (m, 2H); [6.8 (d, J=9Hz) and 6.85 (d, J=9Hz), total 1H]; 7.3 (br d, J=9Hz) and 7.35 (br d, J=9Hz), total 1H], [7.55 (br.s) and 7.6 (br s), total 1H].

PROCEDURE 6

Preparation of the N-(1-(S)-phenylethyl)carbamate derivative of trans-3,4-dihydro-2,2-dimethyl-4-( 2-oxopiperidin-1-yl)-6-pentafluoroethyl-2H-1-benzopyran- 3-ol

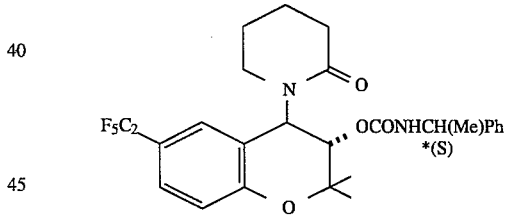

Trans-3,4-dihydro-2,2-dimethyl-4-(2-oxopiperidin-1-yl)-6-pentafluoroethyl)-2H-1-benzopyran-3-ol (1.137 g, 3 mmol) was dissolved in dry toluene (30 ml) and treated with S-(–)-α-methylbenzylisocyanate (0.50 ml, 515 mg, 3.3 mmol). The mixture was refluxed under N$_2$ overnight, cooled and the solvent removed to yeild an oil. This was partially purified by chromatography (Et$_2$O/SiO$_2$) and relevant fractions were purified by further chromatography (20% Et$_2$O/CHCl$_3$, SiO$_2$) to give the pure diastereoisomers. The faster running diastereoisomer was isolated as white crystals m.p. 156°–7° C. (hexane), 680 mg (42%).

$^1$H NMR (CDCl$_3$) δ: 1.32 (s, 3H), 1.41 (s, 3H), 1.51 (d, 3H, J=7Hz), 1.64 (m, 4H), 2.56 (m, 2H), 2.76 (m, 1H), 3.27 (m, 1H), 4.81 (quin, 1H, J=7Hz), 5.07 (d, 1H, J=10.4Hz), 5.19 (d, 1H, J=7.7Hz), 6.19 (d, 1H, J=10.4Hz), 6.93 (d, 1H, J=8.8Hz), 7.19 (s, 1H), 7.3 (m, 6H), [α]$_D^{25}$ (CHCl$_3$) –54.4° (c=0.82).

The slower running diastereoisomer also gave white crystals, m.p. 190°–191° C. (hexane/ethyl acetate), 523 mg (32%).

¹H NMR (CDCl₃) δ: 1.34 (s, 3H), 1.47 (m, 6H), 1.53 (m, 4H), 2.06 (m, 1H), 2.33 (m, 1H), 2.66 (m, 1H), 3.08 (m, 1H), 4.78 (quin, 1H, J=7.2Hz), 5.04 (d, 1H, J=10.5Hz), 5.29 (d, 1H, J=7.7Hz), 6.16 (d, J=10.3Hz), 6.93 (d, 1H, J=8.8Hz), 7.14 (s, 1H), 7.3 (m, 6H).

¹H NMR (DMSO d₆ at 130° C.) δ: 1.26 (3H,s), 1.36 (3H,s), 1.42 (3H, d, J=7Hz), 1.5 (4H, m), 2.15 (1H, m), 2.3 (1H, m), 2.7 (1H, m), 3.2 (1H, m), 4.7 (m, 1H, J=7Hz), 5.07 (1H, d, J=10.2Hz), 5.89 (1H, d, J=10.2Hz), 7.03 (1H, d, J=8.8Hz), 725 (7H, m), 7.46 (1H, dd J: 8.5, 2.2Hz). [α]$_D^{25}$ (EtOH) −20.0° (c=0.48)

PROCEDURE 7

5-Bromo-2-hydroxyacetophenone

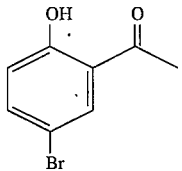

4-Bromophenol (37.5 g, 0.217 mol) was dissolved in water (500 ml) containing sodium hydroxide (10.97 g, 0.274 mol) and acetic anhydride (26.5 ml, 0.285 mol). The solution was stirred for 1 h during which time an oil separated out. The reaction mixture was diluted with carbon tetrachloride (20 ml), separated, washed with sodium bicarbonate solution and then concentrated in vacuo to yield essentially pure 4-bromophenylacetate (48.3 g) as a clear liquid. The crude product was mixed with powdered aluminium chloride (54.7 g, 0.411 mol) and the mixture heated with stirring at 140° C. for 2 h. After the reaction mixture had cooled to 70° C. it was poured into a slurry of ice (200 g) in 2M hydrochloric acid (100 ml). The solution was extracted with dichloromethane (500 ml) and the organics dried and concentrated. Purification was effected by dry flash chromatography on silica (eluent CH₂Cl₂) to yield 5-bromo-2-hydroxyacetophenone (35.6 g, 76% overall) as a light brown solid.

¹H NMR (CDCl₃) δ: 2.65 (s, 3H), 6.95 (d, J=9Hz, 1H), 7.6 (dd, J=9, 2Hz, 1H), 7.9 (d, J=2Hz, 1H), 12.2 (s, 1H).

PROCEDURE 8

6-Bromo-2,2-dimethyl-2H-1-benzopyran-4-one

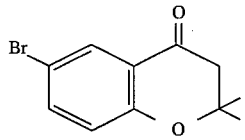

A solution of 5-bromo-2-hydroxyacetophenone (35.07 g, 0.163 mol), acetone (68 ml, 0.926 mol) and pyrrolidine (1.3 ml, 0.155 mol) in benzene (300 ml) was refluxed for 16 h, allowed to cool, diluted with ethyl acetate (300 ml) then washed with dilute hydrochloric acid. The organics were dried and concentrated to a dark solid. Flash chromatography (CH₂Cl₂) yielded 6-bromo-2,2-dimethyl-2H-1-benzopyran-4-one (32.7 g, 78%) as an oil.

¹H NMR (CDCl₃) δ: 1.5 (s, 6H), 2.7 (s, 2H), 6.85 (d, J=9Hz, 1H), 7.6 (dd, J=9, 2Hz 1H), 8.0 (d, J=2Hz, 1H).

PROCEDURE 9

6-Bromo-3,4-dihydro-2,2-dimethyl-2H-1-benzopyran-4-ol

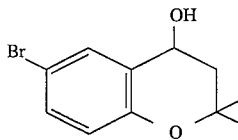

To a solution of 6-bromo-2,2-dimethyl-2H-1-benzopyran-4-one (2.33 g, 9.1 mmol) in methanol (40 ml) was added, portionwise, potassium borohydride (0.49 g, 9.1 mmol). The solution was stirred for 16 h, concentrated and the residues separated between ether and water. The organics were dried and concentrated to a white solid (1.94 g, 83%) m.p. 95° C.

¹H NMR (CDCl₃) δ: 1.25 (s, 3H), 1.35 (s, 3H), 1.8 (dd, J=13, 9Hz, 1H), 1.9 (br.s, 1H), 2.15 (dd, J=13, 6Hz, 1H), 4.8 (m, 1H), 6.75 (d, J=9Hz, 1H), 7.25 (dd, J=9, 3Hz, 1H), 7.55 (d, J=3Hz, 1H).

PROCEDURE 10

6-Bromo-2,2-dimethyl-2H-1-benzopyran

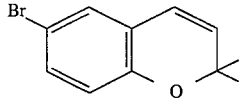

A solution of 6-bromo-3,4-dihydro-2,2-dimethyl-2H-1-benzopyran-4-ol (1.91 g, 7.4 mmol) and p-toluenesulphonic acid (50 mg) in benzene (50 ml) was refluxed in a Dean-Stark apparatus for 18 h, cooled and concentrated. Chromatography of the residue on silica (2:1 petrol/CHCl₃) yielded 6-bromo-2,2-dimethyl-2H-1-benzopyran (1.71 g, 97%) as a yellow liquid.

¹H NMR (CDCl₃) δ: 1.4 (s, 6H), 5.6 (d, J=10Hz, 1H), 6.25 (d, J=10Hz, 1H), 6.75 (d, J=9Hz, 1H), 7.2 (m, 2H).

PROCEDURE 11

2,2-Dimethyl-6-pentafluoroethyl-2H-1-benzopyran

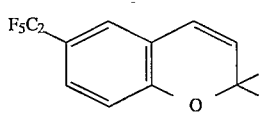

A solution of 6-bromo-2,2-dimethyl-2H-1-benzopyran (1.01 g, 4.24 mmol) in DMF (15 ml)/toluene (6 ml) was heated at 120° C. in a Dean-Stark apparatus, with sodium pentafluoropropionate (1.50 g, 8.06 mmol) and copper (I) iodide (1.64 g, 8.61 mmol) for 1 h until 2 ml of toluene was collected. The apparatus was then rearranged for normal reflux and the mixture heated for a further 4 hr at 155° C. After cooling, the reaction mixture was diluted with ether (80 ml), washed with water, and the mixture filtered through a pad of celite. The organics were separated, washed with brine (3×50 ml), dried and concentrated to an oil. Chromatography on silica (hexane) yielded 2,2-dimethyl-6-pentafluoroethyl-2H-1-benzopyran (0.12 g, 10%) with spectroscopic data identical to that compound produced by procedure 2.

EXAMPLE 1

Trans-3,4-Dihydro-2,2-dimethyl-6-pentafluoroethyl-4-(2-oxopyrrolidin-1-yl)-2H-1-benzopyran-3-ol

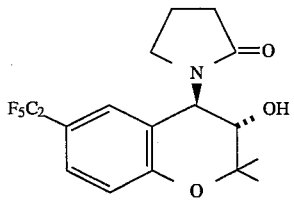

Trans-3-bromo-3,4,-dihydro-2,2-dimethyl-6-pentafluoroethyl- 2H-1-benzopyran-4-ol (0.35 g, 0.93 mmol) was added to a solution of potassium-t-butoxide (0.52 g, 4.64 mmol) in pyrrolidinone (5 ml). The solution was stirred for 3.5 h then diluted with ethyl acetate (50 ml) and hydrochloric acid (30 ml, 2M). The organics were separated, washed with water (4×60 ml), dried (MgSO$_4$) and concentrated to provide trans-3,4-dihydro-2,2-dimethyl-6-pentafluoroethyl-4-(2-oxopyrrolidin- 1-yl)-2H-1-benzopyran-3-ol (0.35 g, 99%), m.p.: 172°–173° C. (ether/hexane).

$^1$H NMR (CDCl$_3$) δ: 1.3 (s,3H); 1.55 (s,3H); 2.1 (m,2H); 2.6 (m,2H); 3.0 (m,1H); 3.3 (m,2H, 1H disappears with D$_2$O) 3.75 (d, J=10Hz, 1H); 5.3 (d, J=10Hz, 1H); 6.9 (d, J=8Hz, 1H); 7.1 (br.s, 1H); 7.4 (br.d, J=8Hz, 1H).

Analysis: Found C, 53.76; H, 4.62; N, 3.77; C$_{17}$H$_{18}$F$_5$NO$_3$ requires: C, 53.85; H, 4.79; N, 3.69%.

EXAMPLE 2

2,2-Dimethyl-6-pentafluoroethyl-4-(2-oxopyrrolidin-1-yl)- 2H-1-benzopyran

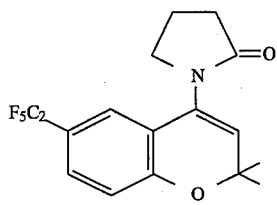

To a solution of trans-3,4-dihydro-2,2-dimethyl-6-pentafluoroethyl- 4-(2-oxopyrrolidin-1-yl)-2H-1-benzopyran-3-ol (0.60 g, 1.58 mmol) and triethylamine (0.24 ml, 1.71 mmol) in tetrahydrofuran (10 ml) was added methanesulphonyl chloride (0.14 ml, 1.81 mmol). The solution was stirred for 4 h, potassium t-butoxide (0.39 g, 3.48 mmol), added and stirring continued for a further 0.5 h. The mixture was poured into ethyl acetate (50 ml)/hydrochloric acid (2M, 20 ml) and the organics separated, washed with sodium bicarbonate solution, dried (MgSO$_4$) and evaporated under reduced pressure to an oil which was chromatographed on silica. Elution with ethyl acetate/hexane (2:1) yielded 2,2-dimethyl-6-pentafluoroethyl-4-(2-oxopyrrolidin- 1-yl)-2H-1-benzopyran as a white solid (0.28 g, 49%), m.p. 94°–95° C.

$^1$H NMR (CDCl$_3$) δ: 1.5 (s, 6H); 2.2 (m, 2H); 2.55 (app.t, J=8Hz, 2H); 3.55 (t, J=7Hz, 2H); 5.7 (s, 1H); 6.9 (d, J=8Hz, 7.1 (d, J=2Hz, 1H); 7.35 (dd, J=8,2Hz, 1H).

Analysis: Found C, 57.36; H, 4.55; N, 3.95; C$_{17}$H$_{16}$F$_5$NO$_2$ requires C, 56.50; H, 4.47; N, 3.88%.

EXAMPLE 3

Trans-3,4-dihydro-2,2-dimethyl-6-(1-hydroxy-2,2,2-trifluoroethyl-4-(2-oxopyrroldin-1-yl)-2H-1-benzopyran- 3-ol

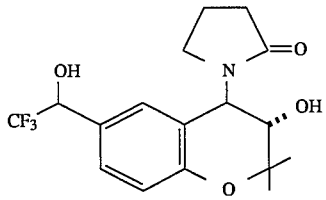

Trans-3-bromo-3,4-dihydro-2,2-dimethyl-6-(1-hydroxy-2,2,2-trifluoroethyl)-2H-1-benzopyran-3-ol (0.306 g, 0.86 mmol) was added to a solution of potassium t-butoxide (0.48 g, 0.43 mmol) in 2-pyrrolidinone (5 ml) and the solution stirred for 3 hrs, diluted with ethyl acetate (50 ml) and poured into hydrochloric acid (20 ml, 2M). The organics were separated, washed with water (3×50 ml), dried (MgSO$_4$), and concentrated to an oil which crystallised from chloroform to yield trans-3, 4-dihydro-2,2-dimethyl-6-(1-hydroxy-2,2,2-trifluoroethyl)- 4-(2-oxopyrrolidin-1-yl)-2H-1-benzopyran-3-ol (0.246 g, 79%) as a 3:2 mixture of diaitereoisomers, m.p. 212°–214° C.

$^1$H NMR (d$_6$-DMSO/CDCl$_3$) δ: 1.2 (s, 3H); 1.45 (s,3H); 2.0 (m, 2H); 2.45 (m, 2H); 2.95 (m, 1H); 3.3 (m, 1H); 3.65 (dd, J=10, 6Hz, 1H); 4.85 (m, 1H); 5.1 (d, J=10Hz, 1H); 5.3 (d, J=6Hz, 1H); 6.45 (1H), [6.75 (d, J=8Hz) and 6.78 (d, J=8Hz)—total 1H]; [6.95 (br.s) and 7.05 (br.s)— total 1H]; [7.2 (d, J=8Hz) and 7.25 (d, J=8Hz)—total 1H].

Accurate Mass: Found 359.1340, C$_{17}$H$_{20}$F$_3$NO$_4$ requires 359.1344.

EXAMPLE 4

Trans-3,4-dihydro-2,2-dimethyl-4-(2-oxopiperidin-1-yl)-6-pentafluoroethyl-2H-1-benzopyran-3-ol

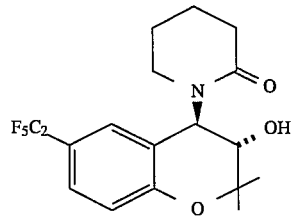

Trans-3-bromo-3,4-dihydro-2,2-dimethyl-6-pentafluoroethyl- 2H-1-benzopyran-4-ol (0.434 g; 1.16 mmol) was added to a solution of potassium t-butoxide (0.651 g, 8.81 mmol) and piperidone (0.584 g, 8.9 mmol) in dimethyl sulphoxide (5 ml). The solution was stirred for 6 hours poured into water (30 ml) and extracted with ethyl acetate. The organics were separated, washed with water (4×50 ml), dried and concentrated. Chromatography over silica (ethyl acetate) yielded trans-3,4-dihydro- 2,2-dimethyl-6-pentafluoroethyl-4-(2-oxopiperidin- 1-yl)-2H-1-benzopyran-3-ol (0.409 g, 90%), m.p. 159°–160° C., (165.5–166.5° C. on recrystallising from hexane/ethyl acetate).

$^1$H nmr (CDCl$_3$) δ: 1.3 (s, 3H); 1.5 (s, 3H); 1.8 (m, 4H); 2.55 (m, 2H); 2.8 (m, 1H); 3.05 (m, 1H); 3.6 (br s 1H); 3.8

(d, J=10Hz, 1H); 5.95 (d, J=10Hz, 1H); 6.9 (d, J=8.5Hz, 1H); 7.2 (br s, 1H); 7.4 (br d, J=8.5 Hz, 1H).

Analysis: Found C, 54.79; H, 5.16; N, 3.63% $C_{18}H_{20}NO_3F_5$ requires C, 54.95; H, 5.13; N, 3.56[{]jf44

EXAMPLE 5

Trans-3,4-dihydro-2,2-dimethyl-6-pentafluoroethyl-4-( 2(1H)-pyridon-1-yl)-2H-1-benzopyran-3-ol

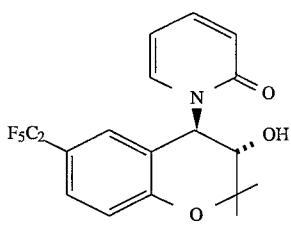

Trans-3-bromo-3,4-dihydro-2,2-dimethyl-6-pentafluoroethyl- 2H-1-benzopyran-4-ol (0.30 g, 0.8 mmol) was added to a solution of potassium t-butoxide (0.448 g, 4 mmol) and 2-pyridone (0.387 g, 4.1 mmol) in dimethyl sulphoxide (5 ml). The solution was stirred for 6 hours, and then diluted with ethyl acetate (70 ml)/water (30 ml). The organics were separated, washed with water (4×50 ml), dried and concentrated. Preparative layer chromatography (3:1 ethyl acetate/hexane) yielded trans-3,4-dihydro-2,2-dimethyl-6-pentafluoroethyl-4-( 2(1H)-pyridon-1-yl)-2H-1-benzopyran-3-ol as a white solid (0.124 g, 40%), m.p. 156°–157° C.

$^1$H nmr (CDCl$_3$) δ: 1.4 (s, 3H); 1.55 (s, 3H); 3.85 (dd, J=9.5 and 4.5Hz, 1H); 4.2 (d, J=4.5Hz, 1H); 6.25 (t, J=6.8Hz, 1H); 6.35 (d, J=9.8Hz, 1H); 6.65 (d, J=9.5Hz, 1H); 6.9 (m, 3H); 7.4 (m, 2H).

Analysis: Found C, 55.72; H, 4.2; N, 3.53% $C_{18}H_{16}NO_3F_5$ requires C, 55.52; H, 4.15; N, 3.60[{]jf44

EXAMPLE 6

(–)-Trans-3,4-dihydro-2,2-dimethyl-4-(2-oxopiperidin-1-yl)-6-pentafluoroethyl-2H-1-benzopyran-3-ol

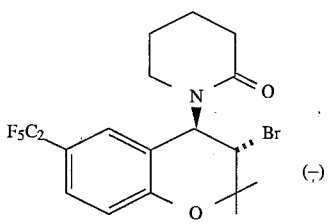

The slower running diastereomeric carbamate from Procedure 6 (850 mg, 1.6 mmol) was combined with dry toluene (20 ml), trichlorosilane (540 mg, 0.42 ml, 4 mmol) and triethylamine (400 mg, 0.55 ml, 4 mmol) under nitrogen. The mixture was stirred overnight at 40° C., then cooled and the toluene evaporated under reduced pressure. The residue was partitioned between ethyl acetate and water, the organic layer washed, dried and evaporated to yield a glass (871 mg) which was chromatographed on silica (EtOAc followed by CH$_2$Cl$_2$/EtOAc) to give the title compound 161 mg (31%), m.p. 143° C. (hexane).

$^1$H NMR (CDCl$_3$) δ: 1.29 (s 3H) 1.53 (s 3H) 1.87 (m 4H), 2.63 (m, 2H), 2.89 (m, 1H), 3.08 (m, 1H), 3.55 (d, 1H, J=5.3Hz), 3.79 (dd, 1H, J$_1$=0.2, J$_2$=5.3Hz), 5.96 (d, 1H, J=10.2Hz), 6.92 (d, 1H, J=8.3Hz), 7.17 (s, 1H), 7.38 (dd, 1H, J$_1$=8.8, J$_2$=1.9Hz).

Analysis: Found C, 55.22; H, 5.14; N, 3.51; $C_{18}H_{20}F_3NO_3$ requires: C, 54.95; H, 5.13; N, 3.56% Mass Spectrum Observed: 393.1359 $C_{18}H_{20}F_3NO_3$ requires: 393.1364 [α]$_D^{25}$ (EtOH, C=0.9)=–56.2°

EXAMPLE 7

(+)-Trans-3,4-dihydro-2,2-dimethyl-4-(2-oxopiperidin-1-yl)-6-pentafluoroethyl-2H-1-benzopyran-3-ol

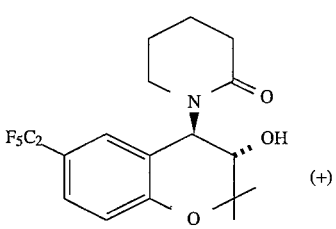

The title compound (240 mg, 34%, mp 142°–3° C.) was prepared and purified in an analogous manner to that of the (–) enantiomer (Example 6) but using the faster running diastereomer of Procedure 6 (910 mg, 1.87 mmol).

$^1$H NMR (CDCl$_3$) δ: 1.28 (s, 3H), 1.52 (s, 3H), 1.88 (m, 4H), 2.59 (s, 2H), 2.88 (m, 1H), 3.08 (m, 1H), 3.75 (m, 2H), 5.96 (d, 1H, J=9.9Hz), 6.92 (d, 1H, J=8.5Hz), 7.14 (bs, 1H), 7.38 (dd, 1H, J$_1$=8.8, J$_2$=1.9Hz).

Analysis: Found C, 55.10; H, 5.11; N, 3.62; $C_{18}H_{20}F_3NO_3$ requires: C, 54.95; H, 5.13; N, 3.56% Mass Spectrum Observed: 393.1359 $C_{18}H_{20}F_3NO_3$ requires: 393.1364 [α]$_D^{25}$ (EtOH, C=1.04)=+57.9°

EXAMPLE 8

2,2-Dimethyl-6-pentafluoroethyl-4-(2-oxopiperidin-1-yl)- 2H-1-benzopyran

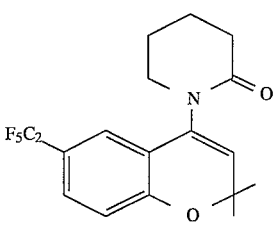

trans-3-Bromo-2,2-dimethyl-6-pentafluoroethyl-2H-1-benzopyran-4-ol (6.0 g, 16 mmol) was added under N$_2$ to a solution of piperidone anion (from piperidone (7.9 g, 80 mmol and potassium t-butoxide (8.96 g, 72 mmol) in DMSO (70 ml). The mixture was stirred for 6 h and then poured into water (500 ml) and left overnight. The product was filtered off, washed and dried to give 5.45 g of a mixture of the title compound and its corresponding chromanol (Example 4). The mixture was crystallized from hexane/EtAc to yield 3.75 g of the chromanol. The residue was separated by chromatography on silica (EtAc and 20% Et$_2$O/CHCl$_3$) to yield a further quantity (70 mg) of chromanol and the title compound (38 mg), m.p. 121°–2° C. (hexane).

$^1$H NMR (CDCl$_3$) δ: 1.52 (bs, 6H), 1.94 (bs, 4H), 2.56 (m, 2H), 3.42 (bs, 2H), 5.64 (s, 1H), 6.90 (d, 1H, J=8.5Hz), 7.15 (d, 1H, J=2.2Hz), 7.35 (dd, 1H, J=8.5, J$_2$=2.2).

Analysis: Found C, 57.63; H, 4.82; N, 3.80; $C_{18}H_{18}F_5NO_2$ requires: C, 57.60; H, 4.83; N, 3.73% Mass Spectrum Observed: 375.1256 $C_{18}H_{18}F_5NO_3$ requires: 375.1258

EXAMPLE 9

2,2-Dimethyl-6-pentafluoroethyl-4-(2(1H)pyridon-1-yl)-2H-1-benzopyran

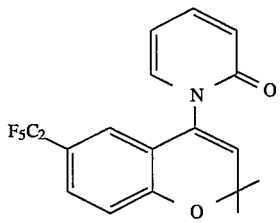

To a solution of trans-3,4-dihydro-2,2-dimethyl-6-pentafluoroethyl-4-(2(1H)pyridon-1-yl)-2H-1-benzopyran-3-ol (0.307 g, 0.79 mmol) and triethylamine (0.12 ml, 0.88 mmol) in tetrahydrofuran (10 ml) was added methanesulphonyl chloride (0.66 ml, 0.88 mmol). The solution was stirred for 5 h after which time t.l.c. analysis showed no more alcohol present. Potassium t-butoxide (0.22 g, 1.96 mmol) was then added and the solution stirred for a further 30 minutes, whereupon it was diluted with ethyl acetate (30 ml) and washed with water. The organics were separated, dried and concentrated to a white solid. Preparative t.l.c. (3:2 ethyl acetate/hexane) yielded 2,2-dimethyl-6-pentafluoroethyl-4-(2(1H)pyridon-1-yl)- 2H-1-benzopyran (0.132 g, 45%) as a white solid, m.p. 128°–129°.

$^1$H NMR (CDCl$_3$) δ: 1.55 (s, 6H), 5.8 (s, 1H), 6.25 (m, 1H), 6.68 (d, J=9Hz, 1H), 6.8 (d, J=2Hz, 1H), 6.9 (d, J=7Hz, 1H), 7.2 (dd, J=7, 2Hz, 1H), 7.45 (m, 2H). Mass Spectrum Observed: 371.0945 $C_{18}H_{14}NO_2F_5$ requires: 371.0945

PHARMACOLOGICAL DATA

1. Bronchodilator Activity (a) Bronchodilation in vitro; guinea pig tracheal spiral preparations Male guinea pigs (300–600 g) were stunned by a blow to the head and bled from the carotid artery. The trachea was exposed, dissected free of connective tissue, and transferred to oxygenated krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with krebs solution at 37° C. and bubbled with 5% $CO_2$ with $O_2$. The resting tension of the preparations was set at 2 g and changes in muscle tension were monitored isometrically by means of a UFI (2 oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2 g using a mechanical micromanipulator system.

Once a steady resting tension had been obtained, the preparations were dosed cumulatively with the test compound ($10^{-8}$–$2\times10^{-5}$M), and finally a maximum relaxation achieved by addition of $10^{-3}$M isoprenaline. The fall in tension evoked by the test compound was expressed as a percentage of the total relaxation evoked in the presence of $10^{-3}$M isoprenaline. Appropriate concentration-relaxation curves were then constructed and values for potency ($IC_{50}$) and efficacy (Intrinsic Activity, I.A.) were obtained.

The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM; pH ca. 7.45.

| | Results | |
|---|---|---|
| Example No. | In vitro $IC_{50}$ (M) | I.A |
| 1 | $1.9 \times 10^{-7}$ | 0.88 |
| 2 | $9.8 \times 10^{-8}$ | 0.96 |
| 3 | $3.7 \times 10^{-7}$ | 0.89 |
| 4 | $6.3 \times 10^{-8}$ | 0.90 |
| 5 | $1.5 \times 10^{-7}$ | 0.97 |
| 6 | $1.9 \times 10^{-8}$ | 0.93 |
| 8 | $1.9 \times 10^{-7}$ | 0.88 |
| 9 | $7.15 \times 10^{-8}$ | 0.84 |

2. Antihypertensive Activity

Blood Pressure Lowering Activity

Systolic blood pressures were recorded by a modification of the tail cuff method described by I. M. Claxton, M. G. Palfreyman, R. H. Poyser, R. L. Whiting, European Journal of Pharmacology, 37,179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >180 mmHg were considered hypertensive.

| Compound of Example No. | Initial | | Dose mg/kg p.o. | % change in systolic B.P. | | |
|---|---|---|---|---|---|---|
| | n | B.P. | | 1 h | 2 h | 4 h |
| 1 | 4 | 284 ± 4 | 0.1 | −19 ± 3 | −30 ± 2 | −28 ± 2 |
| 2 | 3 | 230 ± 3 | 1.0 | −38 ± 2 | −24 ± 10 | −18 ± 6 |
| 3 | 3 | 240 ± 0.7 | 0.3 | −40 ± 10 | −29 ± 7 | −25 ± 7 |
| 4 | 3 | 228 ± 1 | 0.3 | −36 ± 3 | −30 ± 1 | −26 ± 2 |

Toxicology

No toxicological effects were indicated in any of the abovementioned tests.

We claim:

1. A compound of formula (I):

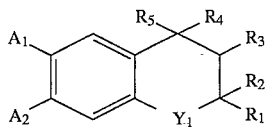

or, where appropriate, a pharmaceutically acceptable salt thereof, or a pharmaceutically acceptable solvate thereof, wherein:

one of $A_1$ or $A_2$ represents hydrogen and the other represents a group $CF_3$—Y— wherein Y represents —$CF_2$ [ >C=O, or —CH(OH)—];

$Y_1$ represents —O—, $R_1$ and $R_2$ independently represent hydrogen or $C_{1-12}$ alkyl; or $R_1$ and $R_2$ together represent a $C_{2-7}$ polymethylene moiety;

$R_3$ represents hydrogen, hydroxy, $C_{1-12}$ alkoxy or $C_{1-12}$ alkylcarbonyloxy and $R_4$ is hydrogen, or $R_3$ and $R_4$ together represent a bond;

$R_5$ represents either a moiety of formula (a):

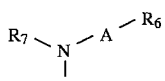

wherein A represents >C=X wherein X is O, S or $NR_8$ wherein $R_8$ represents CN, $NO_2$, $COR_9$ wherein $R_9$ is $C_{1-12}$ alkyl, amino, mono-$C_{1-12}$ alkylamino fluoro $C_{1-2}$ alkyl comprising one or more fluorine atoms, phenyl or phenyl optionally substituted with up to five substituents selected from the group consisting of halogen, $C_{1-12}$ alkyl, phenyl, $C_{1-12}$ alkoxy, halo-$C_{1-12}$-alkyl, hydroxy, amino, nitro, carboxy, $C_{1-12}$ alkoxycarbonyl, $C_{1-12}$ alkoxycarbonylalkyl, $C_{1-12}$ alkylcarbonyloxy and $C_{1-12}$ alkylcarbonyl or $R_8$ is $SO_2R_9$ wherein $R_9$ is as defined above, or A represents a bond; when A represents >C=X wherein X is O or S, then $R_6$ is hydrogen; $C_{1-12}$ alkyl optionally substituted by one or more groups or atoms selected from halogen, hydroxy, $C_{1-12}$ alkoxy, $C_{1-12}$ alkoxycarbonyl, carboxy or an ester or amide thereof, amino, mono-$C_{1-12}$ alkylamino, and di-$C_{1-12}$ alkylamino; $C_{2-12}$ alkenyl; amino optionally substituted by a $C_{1-12}$ alkyl or $C_{2-12}$ alkenyl group or by a $C_{1-12}$ alkanoyl group optionally substituted by up to three halo atoms, by a phenyl group optionally substituted by $C_{1-12}$ alkyl, $C_{1-12}$ alkoxy or halogen; phenyl or naphthyl optionally substituted by 1, 2, 3 or 4 substituents selected from the group consisting of $C_{1-12}$ alkyl, $C_{1-12}$ alkoxy, hydroxy, halogen, fluoro $C_{1-12}$ alkyl comprising one or more fluorine atoms, nitro, cyano, carboxy or an ester thereof, $C_{1-12}$ alkyl carbonyloxy, amino, mono-$C_{1-12}$ alkylamino, and di-$C_{1-12}$ alkylamino; aminocarbonyl, mono-$C_{1-12}$ alkylaminocarbonyl, or di-$C_{1-12}$ alkylaminocarbonyl; or 5- or 6-membered monocyclic heteroaryl moieties selected from the group consisting of furyl, thienyl, pyrrolyl, oxazolyl, thiazolyl, imidazolyl and thiadiazolyl, and pyridyl, pyridazyl, pyrimidyl, pyrrazyl and triazyl or 9- or 10-membered bicyclic heteroaryl groups selected from the group consisting of benzofuryl, benzothienyl, indolyl and indazolyl, quinolinyl and isoquinolinyl and quinazolinyl, optionally substituted by 1, 2, 3 or 4 substituents selected from the group consisting of $C_{1-12}$ alkyl, $C_{1-12}$ alkoxy, hydroxy, halogen, fluoro $C_{1-12}$ alkyl comprising one or more fluorine atoms, nitro, cyano, carboxy or an ester thereof, $C_{1-12}$ alkylcarbonyloxy, amino, mono-$C_{1-12}$ alkylamino, di-$C_{1-12}$ alkylamino, aminocarbonyl, mono-$C_{1-12}$ alkylaminocarbonyl and di-$C_{1-12}$ alkylaminocarbonyl; and $R_7$ represents hydrogen or $C_{1-12}$ alkyl; or $R_6$ and $R_7$ together represent a linking chain of formula —$A_3$—$A_4$—, $A_3$ being attached to the nitrogen atom of the moiety —N—A— and $A_4$ being attached to the group A on the said moiety, and wherein $A_3$ represents a $C_{1-12}$ alkyl- substituted or unsubstituted methylene group, $A_4$ represents 2 or 3 linking members, one of the linking members optionally representing O, S or NR and the other linking members each independently representing a $C_{1-12}$ alkyl- substituted or unsubstituted methylene group; R represents hydrogen, $C_{1-12}$ alkyl, $C_{1-12}$ alkanoyl, phenyl $C_{1-4}$-alkyl, phenylcarbonyl or naphthylcarbonyl optionally substituted with up to five substituents selected from the group consisting of halogen, $C_{1-12}$ alkyl, phenyl, $C_{1-12}$ alkoxy, halo-$C_{1-12}$-alkyl, hydroxy, amino, nitro, carboxy, $C_{1-12}$ alkoxycarbonyl, $C_{1-12}$ alkoxycarbonylalkyl, $C_{1-12}$ alkylcarbonyloxy, and $C_{1-12}$ alkylcarbonyl; or R is furylcarbonyl, thienylcarbonyl or indolylcarbonyl; when A represents >C=X wherein X represents $NR_8$, then $R_6$ represents —$NH.R_{10}$ wherein $R_{10}$ is hydrogen, $C_{1-12}$ alkyl $C_{3-6}$ cycloalkyl, $C_{2-12}$ alkenyl or $C_{2-12}$ alkynyl and $R_7$ is hydrogen or $C_{1-12}$ alkyl; or $R_7$ and $R_{10}$ together represent $C_{2-4}$ polymethylene; when A represents a bond, then $R_6$ and $R_7$ together with the nitrogen atom to which they are attached, form an unsaturated heterocyclic ring having 5 to 7 ring atoms, selected from the group consisting of unsubstituted pyridonyl, pyridonyl substituted with $C_{1-12}$-alkyl, hydroxyl, halogen, alkoxy, alkanoyloxy, nitro, amino, $C_{1-12}$alkylcarbonyl amino, carboxy or alkoxy carbonyl, unsubstituted thiopyridonyl, or thiopyridonyl substituted with $C_{1-12}$-alkyl, hydroxyl, halogen, alkoxy, alkanoyloxy, nitro, amino, $C_{1-12}$alkylcarbonyl amino, carboxy or alkoxy carbonyl, or $R_5$ represents a moiety of formula (c)

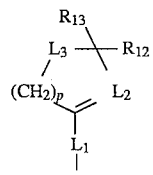

wherein $L_1$ represents O or $NR_{11}$ wherein $R_{11}$ represents hydrogen, $C_{1-12}$alkyl, formyl, acetyl or hydroxymethyl, $L_2$ represents N or $CL_4$ wherein $L_4$ is hydrogen, halogen, formyl or hydroxymethyl, $L_3$ represents $CH_2$, O, S, >$CHL_5$ wherein $L_5$ is halogen or $NL_6$ wherein $L_6$ is hydrogen or $C_{1-12}$ alkyl and $R_{12}$ and $R_{13}$ each independently represent hydrogen or $C_{1-12}$ alkyl or $R_{12}$ together with $R_{13}$ represents oxo or thioxo; and p represents 1, 2 or 3.

2. A compound according to claim 1, wherein $A_1$ represents $CF_3$—Y— and $A_2$ represents hydrogen.

3. A compound according to claim 2, wherein Y represents —$CF_2$— or —CH(OH)—.

4. A compound according to claim 2, wherein Y represents —$CF_2$—.

5. A compound according to claim 1, wherein $R_5$ represents a moiety of formula (a).

6. A compound according to claim 5, wherein A represents >C=X wherein X is O, and $R_6$ together with $R_7$ represents a linking chain —$A_3$—$A_4$—.

7. A compound according to claim 6, wherein $A_4$ represents —$CH_2CH_2$— or —$CH_2CH_2CH_2$—.

8. A compound according to claim 1, wherein $R_6.N.R_7$ represents a piperidonyl group.

9. A compound according to claim 1, wherein the moiety $R_6.N.R_7$ represents unsubstituted pyridonyl.

10. A compound according to claim 1, wherein the moiety $R_6.N.R_7$ represents a 2-pyridon-1-yl group.

11. A compound according to claim 1, wherein A represents >C=X, wherein X represents O or S, or A represents a bond; one of $A_1$ or $A_2$ represents hydrogen the other represents a group $CF_3$ —Y—, wherein Y represents —$CF_2$—, >C=O or —CH(OH)—; $R_1$ and $R_2$ independently represent hydrogen or $C_{1-6}$ alkyl; or $R_1$ and $R_2$ together represent a $C_{2-7}$ polymethylene moiety; $R_3$ represents hydrogen, hydroxy, $C_{1-6}$ alkoxy or $C_{1-12}$ alkylcarbonyloxy and $R_4$ is hydrogen or $R_3$ and $R_4$ together represent a bond; when A represents >C=X, then $R_6$ is hydrogen; $C_{1-6}$ alkyl optionally substituted by halogen, hydroxy, $C_{1-6}$ alkoxy, $C_{1-6}$ alkoxycarbonyl, carboxy or amino optionally substituted by one or two independent $C_{1-6}$ alkyl groups; or $C_{2-6}$ alkenyl; amino optionally substituted by a $C_{1-6}$ alkyl or $C_{2-6}$ alkenyl group of by a $C_{1-6}$ alkanoyl group optionally substituted by up to three halo atoms, by a phenyl group optionally; substituted by $C_{1-6}$ alkyl, $C_{1-6}$ alkoxy or halogen; or phenyl or naphthyl optionally substituted with 1, 2, 3, or 4 substituents selected form the group consisting of $C_{1-12}$ alkyl, $C_{1-12}$ alkoxy, hydroxy, halogen, fluoro $C_{1-12}$ alkyl comprising one or more fluorine atoms, nitro, cyano, carboxy or an ester thereof, $C_{1-12}$ alkylcarbonyloxy, amino, mono-$C_{1-12}$ alkylamino, di-$C_{1-12}$ alkylamino, aminocarbonyl, mono-$C_{1-12}$ alkylaminocarbonyl or di-$C_{1-12}$ alkylaminocarbonyl; or 5- or 6-membered monocyclic heteroaryl moieties selected from the group consisting of furyl, thienyl, pyrrolyl, oxazolyl, thiazolyl, imidazolyl and thiadiazolyl, and pyridyl, pyridazyl, pyrimidyl, pyrrazyl and triazyl or 9- or 10-membered bicyclic heteroaryl groups selected from the group consisting of benzofuryl, benzothienyl, indolyl and indazolyl, quinolinyl and isoquinolinyl and quinazolinyl; either being optionally substituted by one or more groups or atoms selected from the groups or atoms selected from the group consisting of $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups; and $R_7$ represents hydrogen or $C_{1-6}$ alkyl; or $R_6$ and $R_7$ together represent —$CH_2$—$(CH_2)_q$—Z—$(CH_2)_r$— wherein q and r are o to 2 such that q+r is 1 or 2 and z is $CH_2$, O, S, or NR wherein R is hydrogen, $C_{1-9}$ alkyl, $C_{2-7}$ alkanoyl, phenyl $C_{1-4}$ -alkyl, napthylcarbonyl, phenylcarbonyl or benzylcarbonyl optionally substituted in the phenyl or naphthyl ring by one or two or $C_{1-6}$ alkyl, $C_{1-6}$ alkoxy or halogen; or R os furylcarbonyl, thienylcarbonyl or indolycarbonyl; when A represents a bond, then $R_6$ and $R_7$ together with the nitrogen atom to which they are attached, form a substituted or pyridonyl substituted with $C_{1-12}$-alkyl, hydroxyl, halogen, alkoxy, alkanoyloxy, nitro, amino, $C_{1-12}$alkylcarbonyl amino, carboxy or alkoxy carbonyl, or a substituted thiopyridonyl group or thiopyridonyl substituted with $C_{1-12}$-alkyl, hydroxyl, halogen, alkoxy, alkanoyloxy, nitro, amino, $C_{1-12}$ alkylcarbonyl amino, carboxy or alkoxy carbonyl.

12. A compound according to claim 1, wherein $R_1$ and $R_2$ are both methyl.

13. A compound according to claim 1, wherein $R_5$ and $R_3$ are disposed mutually trans with respect to one another.

14. A compound according to claim 1, selected from the group consisting of:

trans-3,4-dihydro-2,2-dimethyl-6-pentafluoroethyl-4-(2-oxopyrrolidin-1-yl)-2H-1-benzopyran-3-ol;

2,2-dimethyl-6-pentafluoroethyl-4-(2-oxopyrrolidin-1-yl)- 2H-1-benzopyran;

trans-3,4-dihydro-2,2-dimethyl-6-(1-hydroxy-2,2,2-trifluoroethyl- 4-(2-oxopyrroldin-1-yl) -2H-1-benzopyran- 3-ol;

trans-3,4-dihydro-2,2-dimethyl-6-pentafluoroethyl-4-( 2-oxopiperidin-1-yl)-2H-1-benzopyran-3-ol;

trans-3,4-dihydro-2,2-dimethyl-6-pentafluoroethyl-4-( 2(1H)-pyridon-1-yl)-2H-1-benzopyran-3-ol;

(−)-trans-3,4-dihydro-2,2-dimethyl-4-(2-oxopiperidin-1-yl) -6-pentafluoroethyl-2H-1-benzopyran-3-ol;

(+)-trans-3,4-dihydro-2,2-dimethyl-4-(2-oxopiperidin-1-yl) -6-pentafluoroethyl-2H-1-benzopyran-3-ol;

2,2-dimethyl-6-pentafluoroethyl-4-(2-oxopiperidin-1-yl)-2H-1-benzopyran; and 2,2-dimethyl-6-pentafluoroethyl-4-(2(1H)-pyridon-1-yl)-2H-1-benzopyran; or a pharmaceutically acceptable salt thereof, or a pharmaceutically acceptable solvate thereof.

15. A compound according to claim 1, being trans-3,4-dihydro-2,2-dimethyl-6-pentafluoroethyl-4-( 2-oxopyrrolidin-1-yl)-2H-1-benzopyran-3-ol or a pharmaceutically acceptable salt thereof or a pharmaceutically acceptable solvate thereof.

16. A compound according to claim 1, being 2,2-dimethyl-6-pentafluoroethyl-4-(2-oxopyrrolidin-1-yl)- 2H-1-benzopyran or a pharmaceutically acceptable salt thereof or a pharmaceutically acceptable solvate thereof.

17. A compound according to claim 1, being trans-3,4-dihydro-2,2-dimethyl-6-(1-hydroxy-2,2,2-trifluoroethyl-4-(2-oxopyrroldin-1-yl)-2H-1-benzopyran- 3-ol or a pharmaceutically acceptable salt thereof or a pharmaceutically acceptable solvate thereof.

18. A compound according to claim 1, being trans-3,4-dihydro-2,2-dimethyl-6-pentafluoroethyl-4-( 2-oxopiperidin-1-yl)-2H-1-benzopyran-3-ol or a pharmaceutically acceptable salt thereof or a pharmaceutically acceptable solvate thereof.

19. A compound according to claim 1, being trans-3,4-dihydro-2,2-dimethyl-6-pentafluoroethyl-4-( 2(1H)-pyridon-1-yl)-2H-1-benzopyran-3-ol or a pharmaceutically acceptable salt thereof or a pharmaceutically acceptable solvate thereof.

20. A compound according to claim 1, being (−)-trans-3, 4-dihydro-2,2-dimethyl-4-(2-oxopiperidin- 1-yl)-6-pentafluoroethyl-2H-1-benzopyran-3-ol or a pharmaceutically acceptable salt thereof or a pharmaceutically acceptable solvate thereof.

21. A compound according to claim 1, being (+)-trans-3, 4-Dihydro-2,2-dimethyl-4-(2-oxopiperidin- 1-yl)-6-pentafluoroethyl-2H-1-benzopyran-3-ol or a pharmaceutically acceptable salt thereof or a pharmaceutically acceptable solvate thereof.

22. A compound according to claim 1, being 2,2-dimethyl-6-pentafluoroethyl-4-(2-oxopiperidin-1-yl)- 2H-1-benzopyran or a pharmaceutically acceptable salt thereof or a pharmaceutically acceptable solvate thereof.

23. A compound according to claim 1, being 2,2-dimethyl-6-pentafluoroethyl-4-(2 (1H)pyridon-1-yl)- 2H-1-benzopyran or a pharmaceutically acceptable salt thereof or a pharmaceutically acceptable solvate thereof.

24. A pharmaceutical composition for the treatment of respiratory tract disorders in mammals, which comprises an effective, non-toxic amount of a compound of formula (I), or a pharmaceutically acceptable salt thereof or a pharmaceutically acceptable solvate thereof, and a pharmaceutically acceptable carrier.

25. A composition according to claim 24, adapted for inhaled administration.

26. A method for the treatment of respiratory tract disorders in mammals, which comprises administering an effective, non-toxic amount of a compound of formula (I), or a pharmaceutically acceptable salt thereof or a pharmaceutically acceptable solvate thereof to the mammal in need thereof.

27. A method of treatment of hypertension and/or for the disorders associated with smooth muscle contraction of the gastro-intestinal tract, cardiovascular disorders and/or in the treatment and/or prophylaxis of disorders associated with pulmonary hypertension and disorders associated with right heart failure and/or in the treatment of epilepsy, in mammals, which comprises administering an effective, non-toxic amount of a compound of formula (I), or a pharmaceutically acceptable salt thereof or a pharmaceutically acceptable solvate thereof to the mammal in need thereof.

28. The composition according to claim 24, wherein said compound is (−)-trans-3,4-dihydro-2,2-dimethyl- 4-(2-oxopiperidin-1-yl)-6-pentafluoroethyl-2H-1-benzoypyran-3-ol or a pharmaceutically acceptable solvate thereof.

29. The method according to claim 26, wherein said compound is (−)-trans-3,4-dihydro-2,2-dimethyl-4-(2-oxopiperidin- 1-yl)-6-pentafluoroethyl-2H-1-benzoypyran-3-ol or a pharmaceutically acceptable solvate thereof.

30. A pharmaceutical composition for the treatment of hypertension and/or disorders associated with smooth muscle contraction of the gastro-intestinal tract, cardiovascular disorders and/or in the treatment and/or prophylaxis of disorders associated with pulmonary hypertension and disorders associated with right heart failure and/or in the treatment of epilepsy, in mammals, which comprises an effective, non-toxic amount of a compound of formula (I), or a pharmaceutically acceptable salt thereof or a pharmaceutically acceptable solvate thereof.

31. A compound according to claim 1, wherein $A_2$ is $CF_3$—Y— and $A_1$ is hydrogen or $A_1$ is hydrogen and $A_2$ is $CF_3C(O)$— or $CF_3CH(OH)$—.

32. A compound of formula (I):

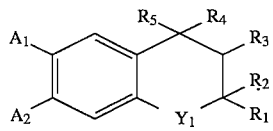

or, where appropriate, a pharmaceutically acceptable salt thereof, or a pharmaceutically acceptable solvate thereof, in the form of a microfine powder wherein: one of $A_1$ or $A_2$ represents hydrogen and the other represents a group $CF_3$—Y— wherein Y represents —$CF_2$—; $Y_1$ represents —O—, $R_1$ and $R_2$ independently represent hydrogen or $C_{1-12}$ alkyl; or $R_1$ and $R_2$ together represent a $C_{2-7}$ polymethylene moiety; $R_3$ represents hydrogen, hydroxy, $C_{1-12}$ alkoxy or $C_{1-12}$ alkylcarbonyloxy and $R_4$ is hydrogen, or $R_3$ and $R_4$ together represent a bond; $R_5$ represents either a moiety of formula (a):

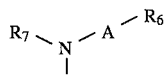

wherein A represents >C=X wherein X is O, S or $NR_8$ wherein $R_8$ represents CN, $NO_2$, $COR_9$ wherein $R_9$ is $C_{1-12}$ alkyl, amino, mono-$C_{1-12}$ alkylamino, fluoro $C_{1-12}$ alkyl comprising one or more fluorine atoms, phenyl or phenyl optionally substituted with up to five substituents selected from the group consisting of halogen, $C_{1-12}$ alkyl, phenyl, $C_{1-12}$ alkoxy, halo-$C_{1-12}$-alkyl, hydroxy, amino, nitro, carboxy, $C_{1-12}$ alkoxycarbonyl, $C_{1-12}$ alkoxycarbonylalkyl, $C_{1-12}$ alkylcarbonyloxyl and $C_{1-12}$ alkylcarbonyl or $R_8$ is $SO_2R_9$ wherein $R_9$ is as defined above, or A represents a bond; when A represents >C=X wherein X is O or S, then $R_6$ is hydrogen; $C_{1-12}$ alkyl optionally substituted by one or more groups or atoms selected from halogen, hydroxy, $C_{1-12}$ alkoxy, $C_{1-12}$ alkoxycarbonyl, carboxy or an ester or amide thereof, amino, mono-$C_{1-12}$ alkylamino, and di-$C_{1-12}$ alkylamino; $C_{2-12}$ alkenyl; amino optionally substituted by a $C_{1-12}$ alkyl or $C_{2-12}$ alkenyl group or by a $C_{1-12}$ alkanoyl group optionally substituted by up to three halo atoms, by a phenyl group optionally substituted by $C_{1-12}$ alkyl, $C_{1-12}$ alkoxy or halogen; phenyl or naphthyl optionally substituted by 1, 2, 3 or 4 substituents selected from the group consisting of $C_{1-12}$ alkyl, $C_{1-12}$ alkoxy, hydroxy, halogen, fluoro $C_{1-12}$ alkyl comprising one or more fluorine atoms, nitro, cyano, carboxy or an ester thereof, $C_{1-12}$ alkyl carbonyloxy, amino, mono-$C_{1-12}$ alkylamino, and di-$C_{1-12}$ alkylamino; aminocarbonyl, mono-$C_{1-12}$ alkylaminocarbonyl, or di-$C_{1-12}$ alkylaminocarbonyl; or 5- or 6-membered monocyclic heteroaryl moieties selected from the group consisting of furyl, thienyl, pyrrolyl, oxazolyl, thiazolyl, imidazolyl and thiadiazolyl, and pyridyl, pyridazyl, pyrimidyl, pyrrazyl and triazyl or 9- or 10-membered bicyclic heteroaryl groups selected from the group consisting of benzofuryl, benzothienyl, indolyl and indazolyl, quinolinyl and isoquinolinyl and quinazolinyl, optionally substituted by 1, 2, 3 or 4 substituents selected from the group consisting of $C_{1-12}$ alkyl, $C_{1-12}$ alkoxy, hydroxy, halogen, fluoro $C_{1-12}$ alkyl comprising one or more fluorine atoms, nitro, cyano, carboxy or an ester thereof, $C_{1-12}$ alkylcarbonyloxy, amino, mono-$C_{1-12}$ alkylamino, di-$C_{1-12}$ alkylamino, aminocarbonyl, mono-$C_{1-12}$ alkylaminocarbonyl and di-$C_{1-12}$ alkylaminocarbonyl; and $R_7$ represents hydrogen or $C_{1-12}$ alkyl; or $R_6$ and $R_7$ together represent a linking chain of formula —$A_3$—$A_4$—, $A_3$ being attached to the nitrogen atom of the moiety —N—A— and $A_4$ being attached to the group A on the said moiety, and wherein $A_3$ represents a $C_{1-12}$ alkyl- substituted or unsubstituted methylene group, $A_4$ represents 2 or 3 linking members, one of the linking members optionally representing O, S or NR and the other linking members each independently representing a $C_{1-12}$ alkyl- substituted or unsubstituted methylene group; R represents hydrogen, $C_{1-12}$ alkyl, $C_{1-12}$ alkanoyl, phenyl $C_{1-4}$ alkyl, phenylcarbonyl or naphthylcarbonyl optionally substituted with up to five substituents selected from the group consisting of halogen, $C_{1-12}$ alkyl, phenyl, $C_{1-12}$ alkoxy, halo-$C_{1-12}$-alkyl hydroxy, amino, nitro, carboxy, $C_{1-12}$ alkoxycarbonyl, $C_{1-12}$ alkoxycarbonylalkyl, $C_{1-12}$ alkylcarbonyloxy and $C_{1-12}$ alkylcarbonyl; or R is furylcarbonyl, thienylcarbonyl or indolylcarbonyl; when A represents >C=X wherein X represents $NR_8$, then $R_6$ represents —$NH.R_{10}$ wherein $R_{10}$ is hydrogen, $C_{1-12}$ alkyl $C_{3-6}$ cycloalkyl, $C_{2-12}$ alkenyl or $C_{2-12}$ alkynyl and $R_7$ is hydrogen or $C_{1-12}$ alkyl; or $R_7$ and $R_{10}$ together represent $C_{2-4}$ polymethylene; when A represents a bond, then $R_6$ and $R_7$ together with the nitrogen atom to which they are attached, form an unsaturated heterocyclic ring having 5 to 7 ring atoms, selected from the group consisting of unsubstituted pyridonyl, pyridonyl substituted with $C_{1-12}$-alkyl, hydroxyl, halogen, alkoxy, alkanoyloxy, nitro, amino, $C_{1-12}$alkylcarbonyl amino, carboxy or alkoxy carbonyl, unsubstituted thiopyridonyl, or thiopyridonyl substituted with $C_{1-12}$-alkyl, hydroxyl, halogen, alkoxy, alkanoyloxy, nitro, amino, $C_{1-12}$alkylcarbonyl amino, carboxy or alkoxy carbonyl, or $R_5$ represents a moiety of formula (c):

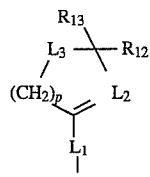

wherein $L_1$ represents O or $NR_{11}$ wherein $R_{11}$ represents hydrogen, $C_{1-12}$ alkyl, formyl, acetyl or hydroxymethyl, $L_2$ represents N or $CL_4$ wherein $L_4$ is hydrogen, halogen, formyl or hydroxymethyl, $L_3$ represents $CH_2$, O, S, $>CHL_5$ wherein $L_5$ is halogen or $NL_6$ wherein $L_6$ is hydrogen or $C_{1-12}$ alkyl and $R_{12}$ and $R_{13}$ each independently represent hydrogen or $C_{1-12}$ alkyl or $R_{12}$ together with $R_{13}$ represents oxo or thioxo; and p represents 1, 2 or 3.

33. A pharmaceutical composition for inhaled administration for the treatment of respiratory tract disorders in mammals, which comprises an effective, non-toxic amount of a compound of formula (I), or a pharmaceutically acceptable salt thereof or a pharmaceutically acceptable solvate thereof, and a pharmaceutically acceptable carrier.

34. The compound according to claim 32 wherein the particle diameter ranges from about 1 to 50 microns.

35. The composition according to claim 33 wherein the particle diameter ranges from about 1 to 50 microns.

36. The composition according to claim 33 in a form suitable for administration by insufflation and suitable for administration in an aerosol as a metered dose or by a breath-activated device.

* * * * *